United States Patent
Fujiwara et al.

(10) Patent No.: US 7,785,636 B2
(45) Date of Patent: *Aug. 31, 2010

(54) INSOLUBLE POWDER, POWDER FOR RESTORING BARRIER FUNCTION OF SKIN, POWDER FOR PREVENTING/MITIGATING SKIN CHAPPING, AND PREPARATION CONTAINING THE SAME FOR EXTERNAL USE ON SKIN

(75) Inventors: Shigeyoshi Fujiwara, Yokohama (JP); Mitsuhiro Denda, Yokohama (JP); Katsuki Ogawa, Yokohama (JP); Tsuyoshi Miyamoto, Yokohama (JP); Sadaki Takata, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 579 days.

This patent is subject to a terminal disclaimer.

(21) Appl. No.: 10/509,539

(22) PCT Filed: Mar. 28, 2003

(86) PCT No.: PCT/JP03/03945

§ 371 (c)(1),
(2), (4) Date: Sep. 28, 2004

(87) PCT Pub. No.: WO03/082228

PCT Pub. Date: Oct. 9, 2003

(65) Prior Publication Data

US 2005/0175645 A1 Aug. 11, 2005

(30) Foreign Application Priority Data

Mar. 28, 2002 (JP) .............................. 2002-091530
Nov. 27, 2002 (JP) .............................. 2002-344179

(51) Int. Cl.
*A61K 33/04* (2006.01)
(52) U.S. Cl. ...................................... 424/709; 106/461
(58) Field of Classification Search .................. None
See application file for complete search history.

(56) References Cited

U.S. PATENT DOCUMENTS

| 5,262,148 | A | | 11/1993 | Sugasawa et al. |
| 5,976,511 | A | | 11/1999 | Ohtsu et al. |
| 6,416,573 | B2 | * | 7/2002 | Horino et al. ............... 106/486 |
| 6,632,276 | B1 | * | 10/2003 | Vogt ........................... 106/417 |

FOREIGN PATENT DOCUMENTS

| CA | 2374539 A1 | * | 11/2000 |
| EP | 0687651 A1 | | 6/1995 |
| EP | 0943324 A2 | | 3/1999 |
| EP | 1375427 A1 | | 3/2002 |
| JP | 05058624 | * | 3/1993 |
| JP | 6-9359 A | | 1/1994 |
| JP | 9-315926 A | | 12/1997 |
| JP | 11-130652 A | | 5/1999 |
| JP | 2002-356415 A | | 12/2002 |
| JP | 2003-12491 A | | 1/2003 |

OTHER PUBLICATIONS

Bloom et al, J. Chem. Soc. A, 1971, p. 833-836.*
Reyerson, L. H. et al. "The Electrokinetic Potentials of Precipitates", pp. 321-332.*
http://www.nbtc.cornell.edu/facilities/downloads/Zeta%20potential%20-%20An%20introduction%20in%2030%20minutes.pdf ("Zeta Potential", technical note, pp. 1-6).*

* cited by examiner

*Primary Examiner*—Robert A Wax
*Assistant Examiner*—Bethany Barham
(74) *Attorney, Agent, or Firm*—Andrews Kurth LLP

(57) ABSTRACT

A first subject of the present invention is an insoluble powder characterized in that a zeta-potential is a negative value.

It is preferable that barium sulfate is a main ingredient in the insoluble powder.

It is preferable that an average primary particle diameter is 3 to 100 μm, and an aspect ratio is 3 to 250 in the insoluble powder.

It is preferable that the insoluble powder is a metal-doped barium sulfate powder obtained by reacting a barium ion and a sulfate ion in the presence of a metal ion.

It is preferable that the metal ion is one or more selected from the group consisting of a lithium ion, a sodium ion and a zinc ion in the insoluble powder.

A second subject of the present invention is a skin barrier function recovering powder, or a skin roughening preventing and improving powder, which comprises the aforementioned powder.

A third subject of the present invention is a skin external composition characterized in that a content of the aforementioned powder is 1 to 40% by weight.

6 Claims, 20 Drawing Sheets

INSOLUBLE POWDER, POWDER FOR RESTORING BARRIER FUNCTION OF SKIN, POWDER FOR PREVENTING/MITIGATING SKIN CHAPPING, AND PREPARATION CONTAINING THE SAME FOR EXTERNAL USE ON SKIN

RELATED APPLICATIONS

This application claims priority to the Japanese Patent Application Nos. 2002-91530 filed on Mar. 28, 2002 and 2002-344179 filed on Nov. 27, 2002 is hereby incorporated with reference for all purposes.

BACKGROUND OF THE INVENTION

1. Field of the Invention

This invention relates to an insoluble powder, in particular, skin barrier function recovering effect and skin roughening preventing and improving effect of the same powder.

2. Prior Art

The skin is anatomically divided to epidermis, derma, and subcutaneous tissue. And said epidermis is composed of basal layer, spinosum layer, granular layer and horny layer. The horny layer of the epidermis is very thin and the thickness is below 20 μm. Accordingly drying and skin roughness are easy to be caused by the external stimulation such as ultraviolet rays, drying, air pollution, and microorganism, and internal factors such as sebum excretion, sweat gland functions, epidermis metabolism, and aging. Hitherto it was carried out that amino acids, polysaccharides, lipids, natural polymeric compounds and so on having high moisturizing effect and water retention effect are blended to skin external composition.

However, the skin external composition that blended a large quantity of these moisturizing agents tends to become sticky, so sometimes happen the harmful effect on use.

On the other hand, it is considered that, if a solid not permeating into the interior of a skin such as a powder can be used as an active ingredient for improving skin roughening, safety can be further enhanced.

The present invention was done in view of the previous problems, and an object thereof is to provide an insoluble powder having excellent skin barrier function recovering effect and skin roughening preventing and improving effect, and a skin external composition containing the same.

SUMMARY OF THE INVENTION

In view of the aforementioned problems, the present inventors intensively studied and, as a result, found that a specified insoluble powder has excellent skin barrier function recovering effect, and skin roughening preventing and improving effect, which resulted in completion of the present invention.

That is, a first subject of the present invention is an insoluble powder characterized in that a zeta-potential is a negative value.

The zeta-potential refers to a part involved in electrophoresis phenomenon among a contact potential difference generated when a liquid is contacted with a solid, and is suitably used for assessing the surface charge state of a subject. A method of measuring the zeta-potential in the present invention is as follows:

A sample was dispersed in a Tris.HCl buffer of pH 7.5, treated by ultrasonic and allowed to stand for 18 hours to obtain a supernatant liquid, which was used for measurement. The zeta-potential was measured by using an electrophoresis light scattering photometer LEZA-600 manufactured by Otsuka Electronics Co., Ltd. Measurement was performed three times, and results were shown as an average value thereof.

It is preferable that barium sulfate is a main ingredient in the insoluble powder.

It is preferable that an average primary particle diameter is 3 to 100 μm, and an aspect ratio is 3 to 250 in the insoluble powder.

In addition, the aspect ratio expresses (average primary particle diameter)/(average thickness).

It is preferable that the insoluble powder is a metal-doped barium sulfate powder obtained by reacting a barium ion with a sulfate ion in the presence of a metal ion.

It is preferable that a mole ratio of the barium ion, the sulfate ion, and the metal ion is 1:0.5 to 2:0.001 to 10 in the insoluble powder.

It is preferable that the metal ion is one or more selected from the group consisting of a lithium ion, a sodium ion and a zinc ion in the insoluble powder.

A second subject of the present invention is a skin barrier function recovering powder, or a skin roughening preventing and improving powder, which comprises the aforementioned powder.

A third subject of the present invention is a skin external composition characterized in that a content of the aforementioned powder is 1 to 40% by weight.

The insoluble powder of the present invention can be used as a skin barrier function recovering agent, and a skin roughening preventing and improving agent.

DESCRIPTION OF THE PREFERRED EMBODIMENT

Preferable embodiments of the present invention will be explained below.

In a normal skin, a calcium ion is localized in a corneum and a dermis, but due to a skin barrier destruction, suitable localization of a calcium ion in a skin is disintegrated, and diffusion of an ion is generated.

The insoluble powder of the present invention is characterized in that a zeta-potential is negative.

Figure 1:
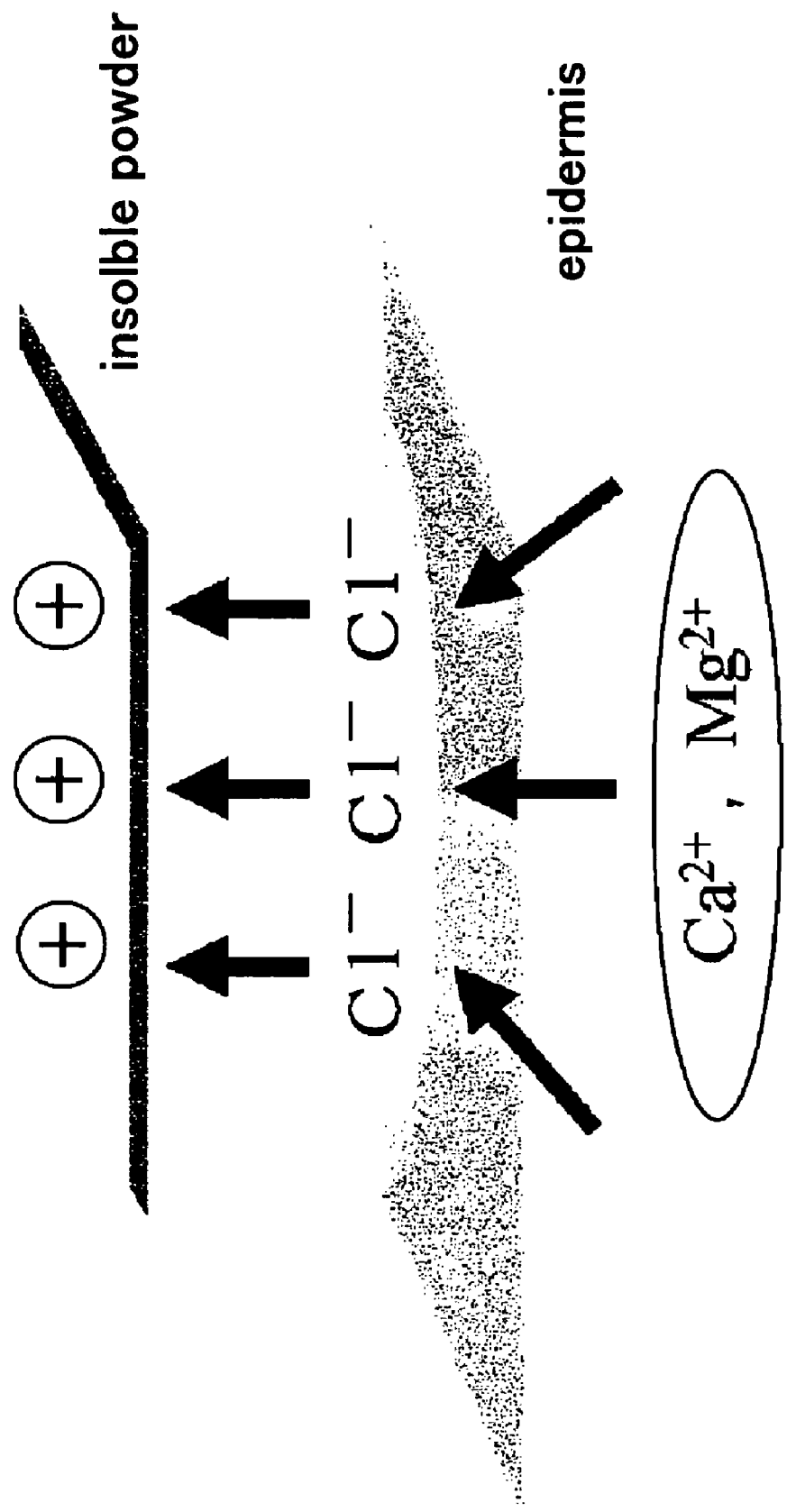
FIG. 1 is a view showing an electric double layer via an epidermis.

When an insoluble powder having a negative zeta-potential is coated on a skin, chloride ion ($Cl^-$) or the like as an anion is attracted to an insoluble powder side. For this reason, calcium ion and magnesium ion ($Ca^{2+}$, $Mg^{2+}$) are localized in an upper layer part of epidermis, in such a manner that those ions are attracted by an anion. That is, an insoluble powder forms a layer of an ion (electric double layer) on a skin (FIG. 1). By formation of an electric double layer via an epidermis, diffusion of a calcium ion and a magnesium ion is suppressed, and skin barrier destruction is recovered.

First Working Mode

A first working mode of the insoluble powder of the present invention is an insoluble powder having an average primary particle diameter of 3 to 100 μm and an aspect ratio of 3 to 250.

When an average primary particle diameter is 3 μm or larger, and an aspect ratio is 3 or larger, since movement of electrons in a particle is difficult to occur, the electric double layer is stabilized and excellent skin barrier recovering effect is obtained. On the other hand, when an average primary particle diameter exceeds 100 μm, or an aspect ratio exceeds 250, usability is deteriorated in some cases when blended in a skin external preparation, being not preferable.

A kind of the insoluble powder used in a first working mode is not particularly limited as far as the aforementioned conditions are satisfied, but examples include barium sulfate.

A barium sulfate powder of the present invention can be prepared by the conventional method such as a method of mixing a barium compound solution containing a barium ion and a sulfate compound solution containing a sulfate ion. A reaction temperature is preferably 50 to 100° C., most preferably 70 to 100° C.

Any barium compound is used as far as it produces a barium ion in a solvent such as water and alcohol, being not particularly limited. For example, barium hydroxide, barium chloride, barium sulfide, barium nitrate, barium acetate and so on are listed. Above all barium chloride and barium hydroxide are desirable, because dispose of the by-product is easy.

Any sulfuric compound is used as far as it produces a sulfuric ion in a solvent such as water and alcohol, being not particularly limited. For example, sulfuric acid, sodium sulfate, sodium hydrogensulfate, ammonium sulfate, potassium sulfate, lithium sulfate and so on are listed. Above all sulfuric acid, sodium sulfate, and ammonium sulfate are desirable.

The barium compound and the sulfate compound are used in the state where they are dissolved in a solvent such as water and alcohol. The concentrations of the barium compound and the sulfate compound are preferably 0.001 to 0.1 mol/L. When the concentration is lower than 0.001 mol/L, efficacy is deteriorated in an industrial process and, when the concentration is higher than 0.1 mol/L, supersaturation occurs, and a number of fine particles are produced, that causes aggregation.

In the first working mode of the present invention, it is preferable that a mole ratio of a barium ion and a sulfate ion is 1:0.5 to 2. When a mole ratio of a sulfate ion is smaller than 0.5, or exceeds 2 relative to a barium ion, efficacy is deteriorated in an industrial process.

Second Working Mode

A second working mode of the insoluble powder of the present invention is a powder of barium sulfate doped with a metal. Barium sulfate doped with a metal has higher skin barrier function recovering effect as compared with non-doped barium sulfate.

A powder of barium sulfate doped with a metal can be prepared by reacting a barium ion with a sulfate ion in the presence of a metal ion. For example, the powder can be prepared by a process of mixing (A) a barium compound solution containing a barium ion and (B) a metal salt compound solution containing a metal ion and, thereafter, adding the mixture to (C) a sulfate compound solution containing a sulfate ion, or a method of adding (A) a barium compound solution containing barium ion and (C) a sulfate compound solution containing sulfate ion to (B) a metal salt compound solution containing a metal ion. A reaction temperature is preferably 50 to 100° C., most preferably 70 to 100° C.

As the barium compound, the sulfate compound, the barium solution, and the sulfate solution, those described in the first embodiment are suitably used.

Examples of a preferable metal ion for doping in the present invention include zinc ion, sodium ion and lithium ion. These can be used alone, or by combining two or more of them. Each metal ion is given as a solution of a metal salt compound in water or alcohol.

As lithium salts, lithium hydroxide, lithium chloride, lithium nitrate, lithium carbonate, lithium acetate, and so on are used.

As sodium salts, sodium hydroxide, sodium chloride, sodium nitrate, sodium carbonate, sodium acetate, and so on are used.

As zinc salts, zinc hydroxide, zinc chloride, zinc nitrate, zinc carbonate, zinc acetate, and so on are used.

In the second embodiment of the present invention, it is preferable that a mole ratio of barium ion, sulfate ion and metal ion is 1:0.5 to 2:0.001 to 10. When a mole ratio of metal ion is smaller than 0.001 relative to barium ion, the effect of the present invention is not sufficiently exerted and, when the ratio exceeds 10, a produced powder of barium sulfate causes aggregation. In addition, when a mole ratio of a sulfate ion is smaller than 0.5, or exceeds 2 relative to barium ion, efficacy is deteriorated in an industrial process.

The insoluble powder of the present invention can be used as a skin barrier function recovering powder, or a skin roughening preventing and improving powder.

When the insoluble powder of the present invention is blended in a skin external preparation, it is preferable that the insoluble powder is contained at 1 to 40% by weight, particularly 8 to 40% by weight relative to a total amount of a skin external preparation. When the amount is smaller than 1% by weight, the effect of the present invention is not sufficiently exerted and, when the amount exceeds 40% by weight, formulation into a preparation becomes difficult.

In addition to the aforementioned essential ingredients, if necessary, additional ingredients which are conventionally used in a cosmetic and/or dermatological region can be appropriately blended in the skin external preparation of the present invention. For example, the skin external preparation may contain, anionic surfactant such as fatty acid soap, alkyl sulfate ester salt, polyoxyethylene alkylether sulfate salt, acyl-N-methyltaurine salt, alkylether phosphate ester salt, N-acyl amino acid salt, organic acid monoglyceride and so on; cationic surfactant such as alkyltrimethylammonium chloride, dialkyldimethylammonium chloride, benzalkonium chloride, alkylpyridinium chloride and so on; ampholytic surfactant such as alkylamidodimethylaminoacetic acid betaine, 2-alkyl-N-carboxy-N-hydroxyimidazolinium betaine, lecithin, enzymatic hydrolysis lecithin and so on; nonionic surfactant such as alkylpolyoxyethylene type, polyhydric alcohol ester type, alkyl polyglucoside type, alkyl polyglycerol type, sugar ester type, polyethylene oxide polypropylene oxide copolymer type, sorbitan fatty acid ester, dimethicone copolyol and so on; moisturizing agent such as glycerin, propylene glycol, 1,3-butylene glycol, polyethylene glycol, sorbitol, sodium lactate, sodium 2-pyrrolidone-5-carboxylate, and sodium hyaluronate; synthetic polymer such as carboxyvinyl polymer, and polyvinyl pyrrolidone; semisynthetic polymer such as carboxymethylcellulose, and hydroxy propyl cellulose; natural polymer such as xanthan gum, dextran, hyaluronic acid, casein, and collagen; ultraviolet absorber such as high molecular weight silicone, benzophenone derivative, p-aminobenzoic acid derivative, methoxycinnamon acid derivative; antioxidant such as tocopherol, BHT; sequestering agent such as EDTA, citric acid, hexametaphosphoric acid, pyrosulfurous acid; minute emulsion such as silicone micro emulsion, high pressure emulsified micro emulsion; and alcohol.

Furthermore as active substances, for example, whitening agent such as arbutin, ascorbic acid and its derivatives; anti-aging agent such as retinol and its derivatives; alpha-hydroxy acids such as lactic acid, and glycolic acid; hair growing agents; vitamins; antiinflammatory agents; germicides; various salts and so on can be included.

Further, its use form is also arbitrary, and in addition to skin lotion, cream, emulsion, lotion, pack, ointment, mousse and soup, makeup cosmetics such as foundation, eye shadow, stain and black ring covering, lip cream, mascara, lipstick, body makeup product, hair rinse, shampoo, skin anti-sunburn cream, and sunburn cream can be used and, further, any forms such as dermatological ointment and bath medicine may be used as far as they are previously used in a cosmetic and/or dermatological region.

In the following, the present invention will be explained by using specific examples. However, the present invention should not be restricted thereto. Unless otherwise stated, quantities are expressed as percent by weight.

First, in order to investigate the insoluble powders in Table 1 for skin barrier function recovering effect, the following experiment was performed.

Method of Measuring Skin Barrier Function Recovery Rate

1. A transdermal evaporating water level (TEWL) on a hairless mouse back was measured with a water evaporation level measuring apparatus (Meeco). This value is defined as recovery rate of TEWL 100%.

2. Skin barrier destruction treatment was carried out by of peeling off an epidermis corneal layer of the whole back of a hairless mouse with a cellophane tape until a TEWL value became 800 to 900 (8 to 9 mg/cm$^2$/hour). A value obtained by subtracting a TEWL value before peeling from a TEWL value immediately after peeling of an epidermis corneal layer is defined as recovery rate of TEWL 0%.

Figure 2:
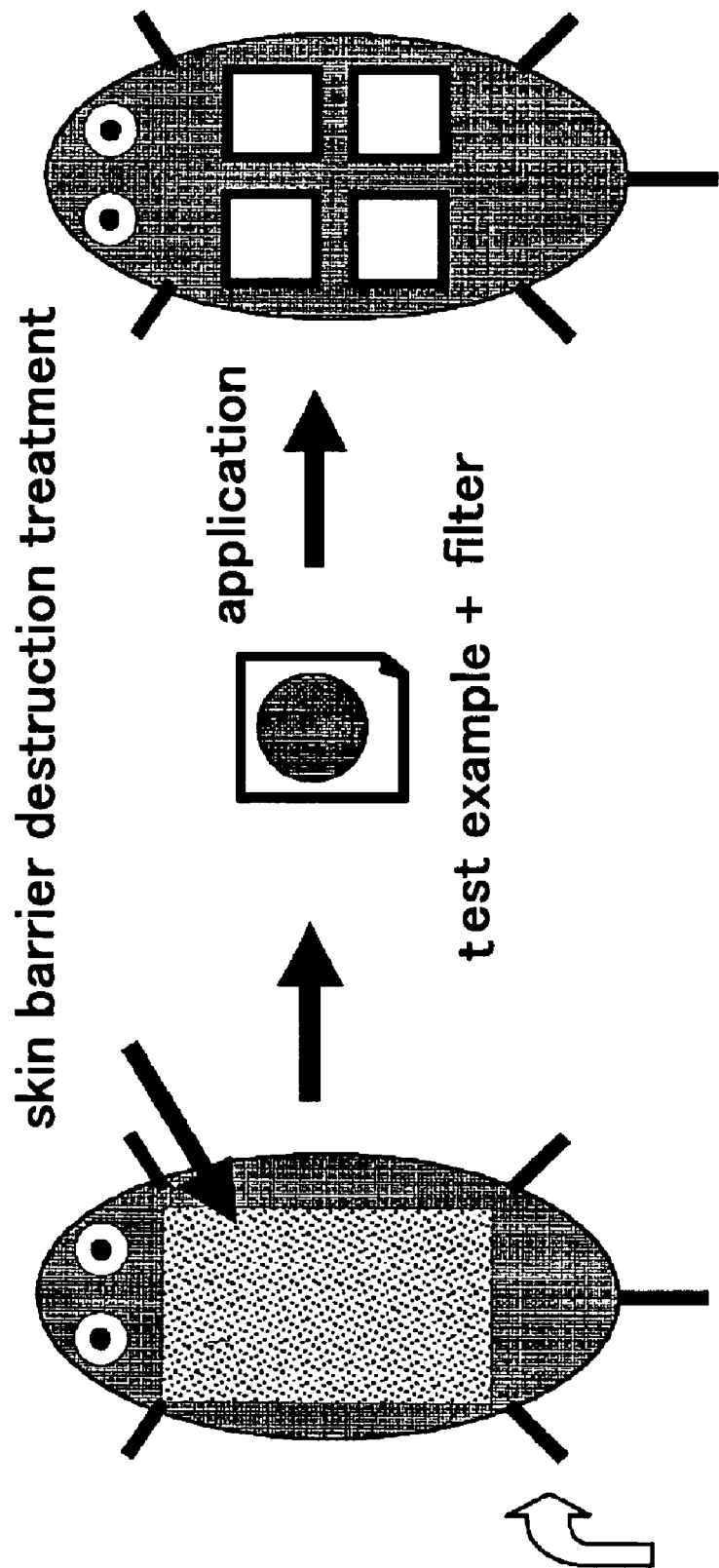
FIG. 2 is a view for illustrating a method of measuring skin barrier function recovering effect.

3. 20 mg of each powder in the following Table 1 was suspended in 100 to 200 μL of ion-exchanged water to prepare a suspension. The suspension was added dropwise to a 2 cm square of a filter placed on a plastic wrap to wet it. This was applied to a back of a hairless mouse immediately after the aforementioned skin barrier destruction treatment so that the added dropwise surface was contacted with the back, and was peeled off after 10 minutes (FIG. 2). In addition, as a control, a filter wetted with an ion-exchanged water was applied to other place on a back of the hairless mouse, and was peeled off after 10 minutes.

4. TEWL on a back of the hairless mouse was measured immediately after peeling (after 0 hour), and after 2, 4 and 6 hours based on a time at which the filter was peeled, and each recovery rate was calculated according to the following equation.

$$\text{Recovery rate}(\%) = 100 \times \left\{ 1 - \left( \frac{TEWL \text{ every hour after corneal layer removal} - TEWL \text{ before corneal layer removal}}{TEWL \text{ immediately after corneal layer removal} - TEWL \text{ before corneal layer removal}} \right) \right\}$$

It can be said that as a recovery rate, in particular, a recovery rate at an early period is better, skin barrier function recovering effect is higher.

Skin barrier function recovering effect is assessed by the following criteria.

Assessment Criteria

○: As compared with the case where ion-exchanged water was used, a recovery rate after two hours is as high as 15% or higher, and a recovery rate is superior also after 6 hours.

Δ: As compared with the case where ion-exchanged water was used, there is no difference in a recovery rate.

X: As compared with the case where ion-exchanged water was used, a recovery rate is inferior.

TABLE 1

| Example | Insoluble powder | Shape | zeta-potential (mV) | Recovery effect |
|---|---|---|---|---|
| 1 | Barium sulfate | plate-like state | −3.69 | ○ |
| 2 | Lithium doped barium sulfate | plate-like state | −2.34 | ○ |
| 3 | Barium sulfate | undefined state | 1.11 | Δ |
| 4 | Iron doped barium sulfate | fir-like state | 0.59 | X |
| 5 | Aluminum doped barium sulfate | plate-like state | 3.08 | Δ |

A method of measuring the zeta-potential in the present invention is as follows:

A sample was dispersed in a Tris.HCl buffer having of pH 7.5, treated by ultrasonic and allowed to stand for 18 hours to obtain a supernatant liquid, which was used for measurement. The zeta-potential was measured by using an electrophoresis light scattering photometer LEZA-600 manufactured by Otsuka Electronics Co., Ltd. Measurement was performed three times, and the results were shown as an average value thereof.

From Examples 1 and 2, it is seen that a powder having a plate-like shape has higher skin barrier function recovering effect. In addition, from Examples 3 and 4, it is seen that a powder having an undefined or fir-like shape or the like other than plate-like shape has no recovering effect, or delays recovery. However, from Example 5, it is thought that since a powder having a plate-like shape has low recovering effect in some cases, a negative zeta-potential value is required in addition to a shape of plate-like.

Considering that barium sulfate is substantially insoluble in water, and that the shape is necessary to be plate-like, it is necessary that a powder of the present invention is insoluble in an aqueous system.

The reason why skin barrier destruction is recovered by coating of an insoluble powder having a plate-like shape and having the negative zeta-potential value, can be contemplated as follows:

When an insoluble powder having a negative zeta-potential is coated on a skin, chloride ion ($Cl^-$) or the like as an anion is attracted to an insoluble powder side. For this reason, calcium ion and magnesium ion ($Ca^{2+}$, $Mg^{2+}$) are localized at an upper layer part of an epidermis in such a manner that those ions are attracted by an anion. That is, an insoluble powder forms a layer of ion (electric double layer) on a skin (FIG. 1). By formation of an electric double layer via an epidermis, diffusion of calcium ion and magnesium ion is suppressed, and skin barrier destruction is recovered.

It is considered that, unless a shape of an insoluble powder is plate-like, its aggregate has many lattice defects and movement of electrons in a particle occurs and, since the electric double layer is unstable, skin barrier function recovering effect is low, while if a shape is plate-like, movement of electrons in a particle does not occur, and the powder has excellent skin barrier function recovering effect.

Kinesis of Intradermal Calcium Ion

Using powders in the aforementioned Table 1, kinesis of calcium ion in a skin during a process of skin barrier recovery was observed.

The whole back of a hairless mouse was subjected to skin barrier destruction treatment with acetone. 40 mg of each powder was suspended in 200 to 400 μL of ion-exchanged water to prepare a suspension. The suspension was added dropwise to a 2×4 cm square of a filter paper placed on a plastic wrap to wet it. This was applied to a back of a hairless mouse that had been subjected to the aforementioned skin barrier destruction treatment so that the added dropwise surface was contacted with the back, and was peeled off after 10 minutes (FIG. 2). A skin on a back of a hairless mouse was taken after 2 hours, and calcium ion was visualized to confirm ion distribution.

A method of visualizing calcium ion is a method of contacting a frozen tissue piece with a water-soluble gel or a plastic containing calcium green 1™ which can color and detect calcium ion under the constant condition to color a calcium green 1™ and the details are described in JP-A No. 2001-324502.

In a skin after skin barrier destruction treatment, diffusion of calcium ion into an epidermis occurred.

Thereafter, a skin on which the powder of Examples 1 or 2 was coated, was recovered into the normal ion localized state, while in a skin coated with the powder of any one of Examples 3 to 5, diffusion of ion was deteriorated. From the foregoing, it was demonstrated that since the insoluble powder of the present invention normalizes intradermal ion distribution, it exerts skin barrier function recovering effect.

Figure 3:
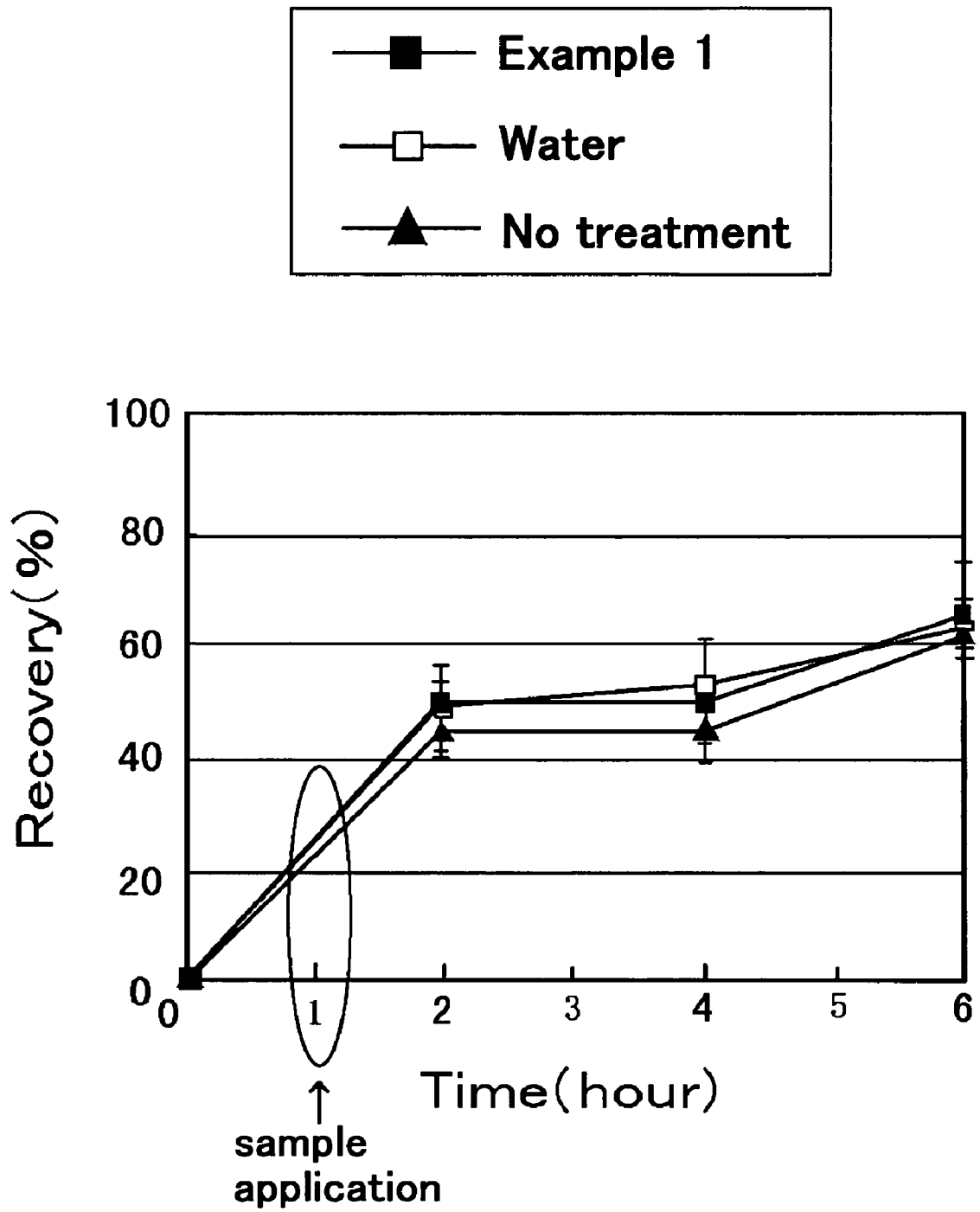
FIG. 3 is a view showing skin barrier recovering effect of the case where a skin barrier was destructed and, after a while, an insoluble powder was coated.

Relationship Between Time Until Powder Application and Skin Barrier Function Recovering Effect Then, after skin barrier destruction, the relationship between time to powder application and recovery effect is investigated. 20 mg of the powder of Example 1 in the Table 1 was suspended in 100 to 200 μL of ion-exchanged water to obtain a suspension, which was coated similarly 1 hour after the aforementioned skin barrier destruction, and recovery rate was calculated every hour. The result of comparison between no treatment after barrier destruction and the case of water coating is shown in FIG. 3.

In the case where application was performed after 1 hour passed, even when the powder of Example 1 having a plate-like shape and a negative zeta-potential value was used, skin barrier function recovering effect could not be obtained. Thereby, it was confirmed that unless a powder is applied immediately after skin barrier destruction, the effect is not manifested. This demonstrates that skin barrier function recovering effect of the insoluble powder of the present invention is closely related to barrier repair mechanism that rapidly occurs in an epidermis corneal layer after barrier destruction. In addition, it was also confirmed that it is not misunderstood that since an amount of water evaporation is reduced due to physical skin clogging by the insoluble powder, skin barrier recovery occurs.

Then, the present inventors further studied.

Zeta-potential

In order to investigate a suitable zeta-potential regarding the insoluble powder of the present invention, the following experiment is performed.

According to the aforementioned method of measuring skin barrier function recovery rate, regarding each plate-like powder in the following Table 2, a skin barrier function recovery rate was measured, and skin barrier function recovering effect was tested.

TABLE 2

| Example | Insoluble powder | zeta-potential (mV) | Shape | Recovery effect |
|---|---|---|---|---|
| 6 | Barium sulfate | −2.31 | plate-like | ◯ |
| 7 | Barium sulfate | −3.31 | plate-like | ◯ |
| 8 | Barium sulfate | −3.69 | plate-like | ◯ |
| 9 | Lithium doped barium sulfate | −2.34 | plate-like | ◯ |
| 10 | Sodium doped barium sulfate | −1.71 | plate-like | ◯ |
| 11 | Magnesium doped barium sulfate | 0.41 | plate-like | X |
| 12 | Aluminum doped barium sulfate | 3.08 | plate-like | Δ |

In Examples 6 to 10 in which an insoluble powder having the negative zeta-potential value was used, the result of high skin barrier function recovering effect was obtained. On the other hand, in Examples 11 and 12 in which an insoluble powder having the positive zeta-potential value was used, recovering effect was not observed.

From the foregoing, it is necessary that the zeta-potential of the insoluble powder of the present invention is a negative value.

Definition of Plate-like

As described above, it is considered to be necessary that the insoluble powder of the present invention has a plate-like shape. Then, in order to define "plate-like", further, the following experiment was performed to investigate a suitable particle diameter and aspect ratio.

According to the aforementioned method of measuring skin barrier function recovery rate, regarding each powder in the following Table 3, a skin barrier function recovery rate was measured, and skin barrier function recovering effect was tested.

TABLE 3

| Example | Insoluble powder | Average primary particle diameter (μm) | aspect ratio | Recovery effect |
|---|---|---|---|---|
| 13 | Barium sulfate | 0.05 | — | X |
| 14 | Barium sulfate | 0.1 | — | X |
| 15 | Barium sulfate | 0.8 | — | Δ |
| 16 | Barium sulfate | 2.0 | — | Δ |
| 17 | Barium sulfate | 3 to 10 | 3 to 20 | ○ |
| 18 | Barium sulfate | 3 to 15 | 3 to 30 | ○ |
| 19 | Barium sulfate | 3 to 20 | 3 to 40 | ○ |
| 20 | Lithium doped barium sulfate | 5 to 20 | 5 to 100 | ○ |
| 21 | Sodium doped barium sulfate | 30 to 50 | 30 to 250 | ○ |

An aspect ratio expresses (average primary particle diameter)/(average thickness).

In Examples 13 to 16 where a powder having an average primary particle diameter of smaller than 3 μm was used, even when the zeta-potential was negative, recovering effect was not observed, and recovery was delayed in some cases. In addition, since it is difficult to make a powder having a small particle diameter plate-like, an aspect ratio could not be measured.

On the other hand, it was confirmed that in Examples 17 to 21 in which a powder having an average primary particle diameter of 3 μm or larger and an aspect ratio of 3 or more was used, recovering effect is high.

In addition, when an average primary particle diameter exceeds 100 μm, or an aspect ratio exceeds 250, usability is deteriorated in some cases when blended in a skin external preparation.

Thereby, it is necessary that the plate-like insoluble powders of the present invention have an average primary particle diameter of 3 to 100 μm, and an aspect ratio of 3 to 250.

Skin Roughening Preventing and Improving Effect

Further, in order to test roughening preventing and improving effect of the insoluble powder of the present invention, the following experiment was performed.

Method of Measuring Thickness of Skin

1. A hairless mouse is pre-bred for 2 days under the drying condition of a humidity of 10% or lower and room temperature of about 25° C. A transdermal evaporating water level (TEWL) on a back of a hairless mouse was measured with a water evaporation amount measuring apparatus (Meeco). This value is defined as a recovery rate of TEWL 100%.

2. Skin barrier destruction treatment was performed by rubbing an epidermis corneal layer on the whole back of a hairless mouse with a cotton swab containing acetone until a TEWL value became 200 to 300 (2 to 3 mg/cm$^2$/hour).

3. 40 mg of each powder of Examples 13 to 19 in the Table 3 was suspended in 200 to 400 μL of ion-exchanged water to prepare a suspension. The suspension was added dropwise to a 2×4 cm square of a filter placed on a plastic wrap to wet it. This was applied to a back of a hairless mouse immediately after the aforementioned skin barrier destruction so that the added dropwise surface was contacted with the back, and was peeled after 10 minutes (FIG. 2).

4. Thereafter, the mouse was bred under the aforementioned drying condition, a skin on a back of a hairless mouse after 48 hours was taken, fixed in 10% formalin, embedded with paraffin, and cut into 2 μm pieces, and thickness thereof was measured with a microscope.

In addition, a hairless mouse which had not subjected to skin barrier destruction treatment and powder coating (Control Example 1) and a hairless mouse which had been subjected to only skin barrier destruction treatment, and had not been subjected to powder coating (Comparative Example 1) were placed under the similar drying and, thereafter, thickness of a skin was measured. When thickness of a skin was increased, it was determined that epidermis proliferating property abnormality occurred and skin roughening occurred.

Figure 4:
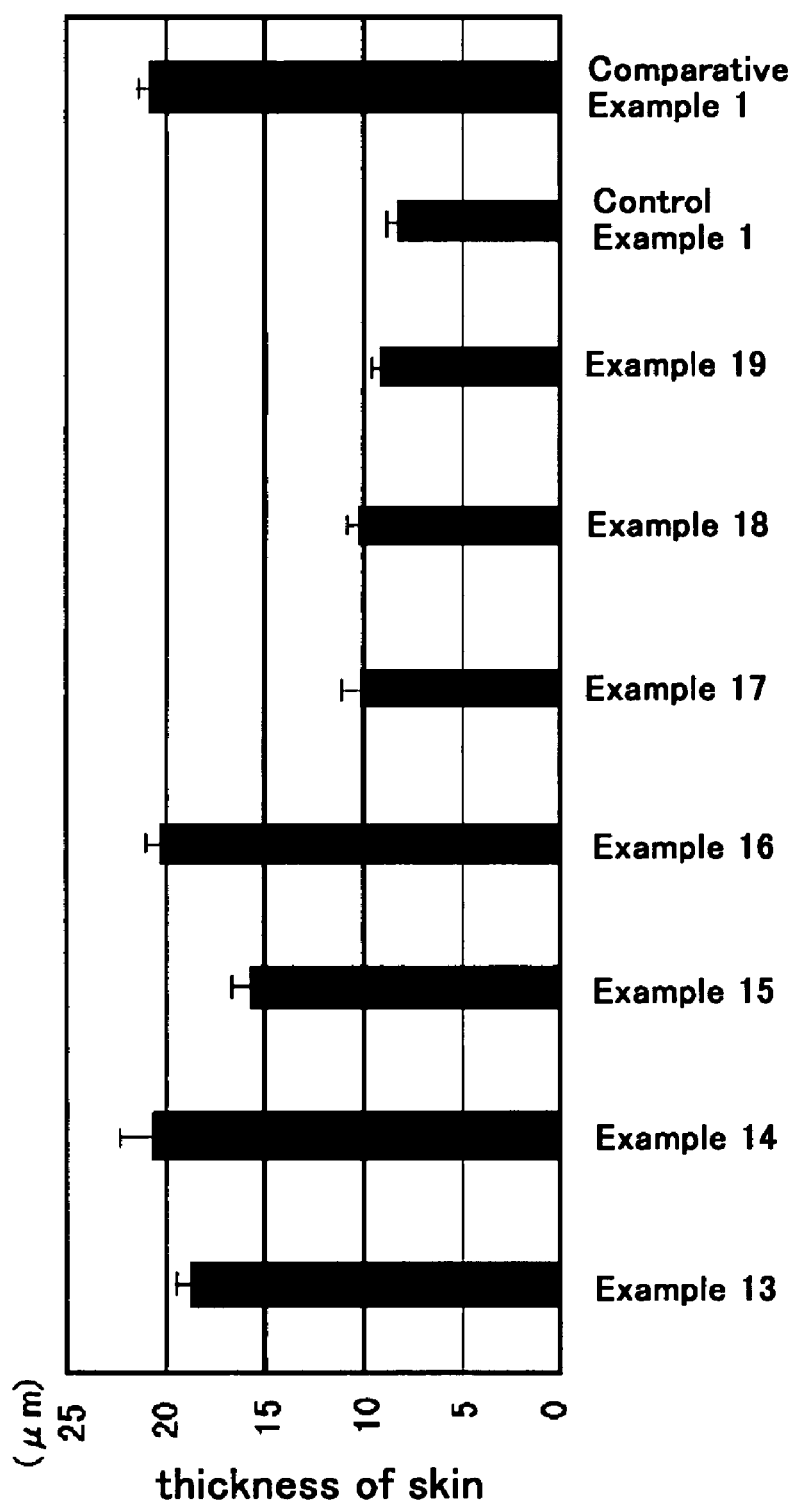
FIG. 4 is a view of comparison of epidermis proliferating property abnormality preventing effect.

Results are shown in FIG. 4.

It was confirmed that in Examples 17 to 19, as compared with Comparative Example 1 in which a powder is not coated, epidermis proliferating property abnormality is remarkably prevented, and this is approximately equivalent to Control Example 1 in which skin barrier destruction is not performed. On the other hand, in Examples 13 to 16, epidermis proliferating property abnormality was not prevented at all.

In addition, as compared with Comparative Example 1, it was observed with naked eyes that skin roughening was further exacerbated in Examples 13 to 16, while it was observed that skin roughening was suppressed in Examples 17 to 19. Thereby, it was confirmed that the insoluble powder having an average primary particle diameter of 3 to 100 μm, an aspect ratio of 3 to 250, and the zeta-potential being a negative value has excellent skin roughening preventing and improving effect.

Skin Barrier Function Recovering Effect of Skin External Preparation (Mouse Test)

Then, using a foundation in which the insoluble powder of the present invention was blended, skin barrier function recovering effect was tested.

According to the aforementioned method of measuring a skin barrier function recovery rate, regarding each powdery foundation of the formulation shown in the following Table 4, a skin barrier function recovery rate was calculated, and this was compared with a hairless mouse which had not been subjected to treatment after skin barrier destruction. It can be said that as a recovery rate, in particular, a recovery rate at an early time zone is better, skin barrier function recovering effect is higher.

Figure 5:
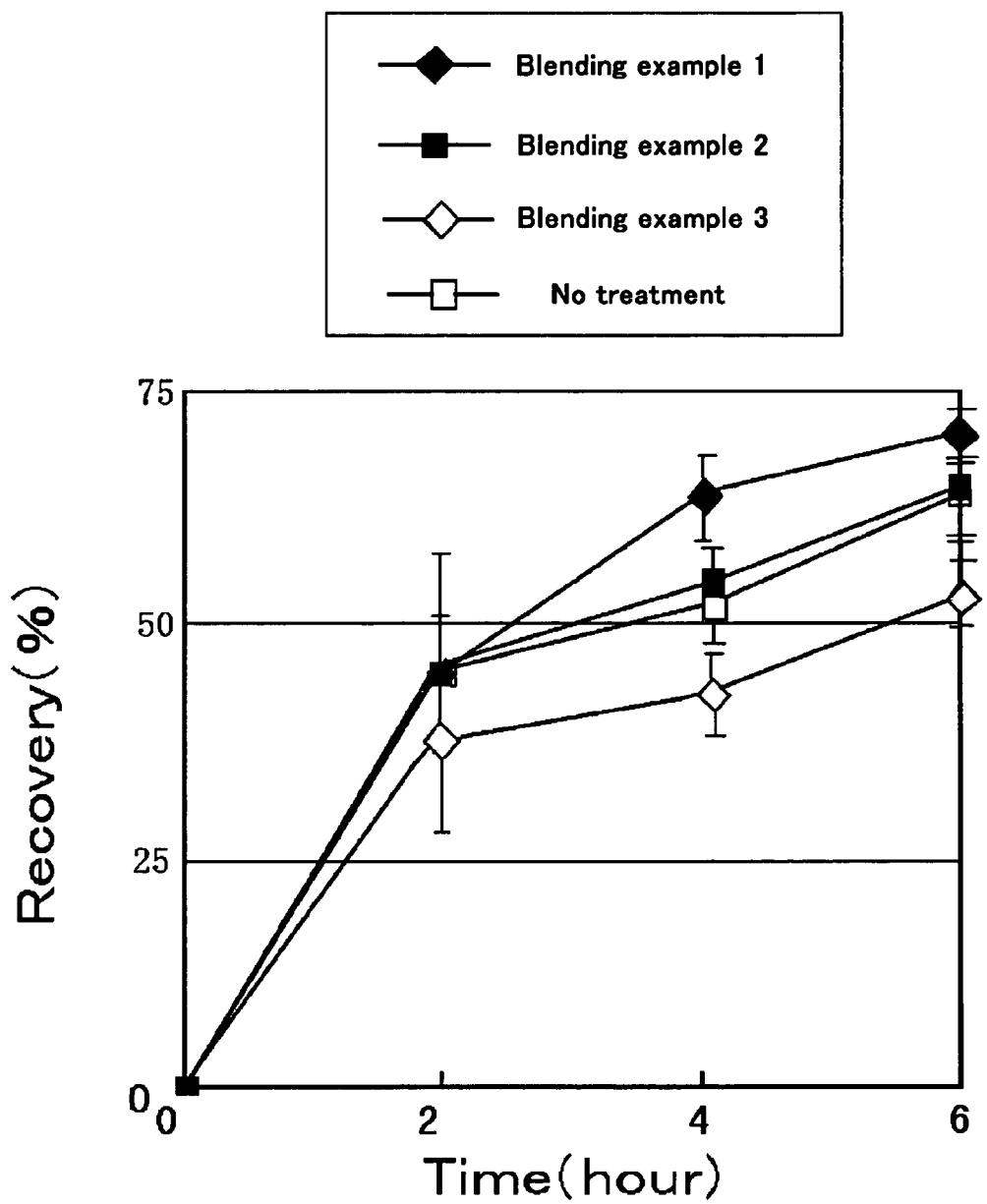
FIG. 5 is a view showing skin barrier recovering effect of a skin external preparation in which each blending amount of an insoluble powder was blended therein.

Results are shown in FIG. 5 (n=9).

TABLE 4

| | Blending example | | |
|---|---|---|---|
| | 1 | 2 | 3 |
| Insoluble powder of Example 7 | 12 | 8 | 0 |
| Metal soap treated talc (TALK ACS-515 ™) | 18.52 | 14.52 | 10.52 |
| Silicone treated mica (SNP-WEY-(S) ™) | 15 | 15 | 15 |
| Silicone treated sericite (SNH-300ST ™) | 22 | 22 | 22 |

TABLE 4-continued

| | Blending example | | |
|---|---|---|---|
| | 1 | 2 | 3 |
| Silicone treated synthesis mica (SNH-ST(EF) ™) | 4 | 4 | 4 |
| Silicone treated titanium oxide (SNH-R-KB-1 ™) | 6 | 6 | 6 |
| Spherical PMMA powder (MICROSFER M-330 ™) | 6 | 6 | 6 |
| Spherical PMMA covering mica (COMPOSITE M-P ™) | 7 | 7 | 7 |
| Silicone treated fine particle titanium oxide (TITANIUM OXIDE MT-020 ™) | 4 | 4 | 4 |
| Silicone treated iron oxide + Silicone treated talc (SNP-R-1(N) ™) | 1.34 | 1.34 | 1.34 |
| Silicone treated iron oxide + Silicone treated talc (SNP-Y-75(N) ™) | 3.32 | 3.32 | 3.32 |
| Silicone treated iron oxide + Silicone treated talc (SNP-BL-1(N) ™) | 0.4 | 0.4 | 0.4 |
| Ethyl paraben | 0.4 | 0.4 | 0.4 |
| Dimethylsilicone(SILICONE KF-96A-6 ™) | 5 | 5 | 5 |
| Glycerol trioctanoate (RA-G-308 ™) | 3 | 3 | 3 |
| Octyl methoxy cinnamate | 3 | 3 | 3 |
| Sorbitan sesuquiisostearate (ESTEMOL 182 ™) | 1 | 1 | 1 |
| Vitamin E (E-mix D ™) | 0.02 | 0.02 | 0.02 |
| | 100 | 100 | 100 |

In a mouse coated with Blending example 2 containing 8% by weight of the insoluble powder of the present invention or Blending example 1 containing 12% by weight of the powder, a recovery rate of TEWL was higher as compared with non-treated mouse. In addition, as a content of a powder was higher, a recovery rate was higher. However, in a mouse coated with Blending example 3 not containing the insoluble powder of the present invention, a recovery rate was deteriorated as compared with a non-treated mouse. Therefore, it was confirmed that a skin external preparation containing the insoluble powder of the present invention has skin barrier function recovering effect, and it is suggested that a preferable content of the insoluble powder in a skin external preparation is 1 to 30% by weight, in particular 8 to 30% by weight.

Skin Barrier Function Recovering Effect of Skin External Preparation (Human Test)

Then, using a foundation in which the insoluble powder of the present invention is blended, skin barrier function recovering effect to a human was tested.

Figure 6:
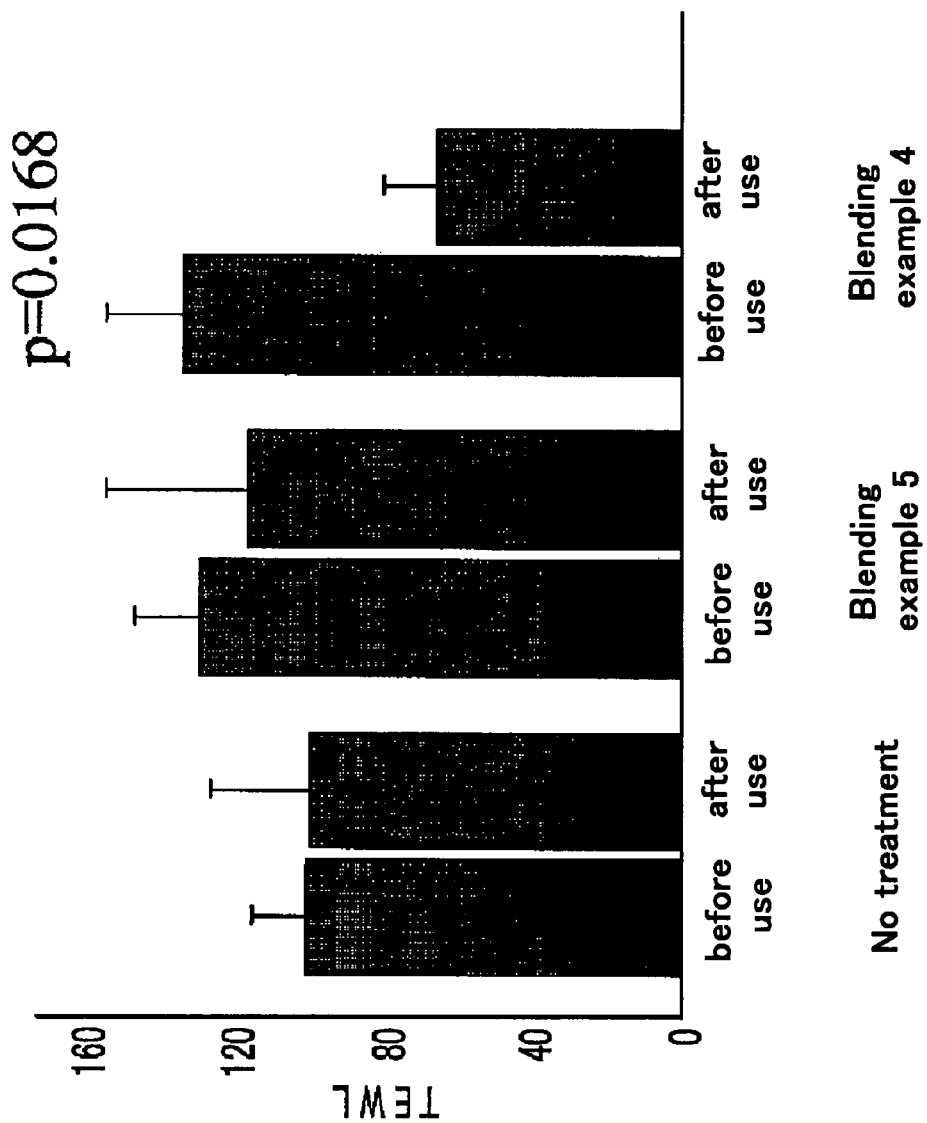
FIG. 6 is a view showing skin barrier recovering effect after application of each skin external preparation to a human.
Figure 7:
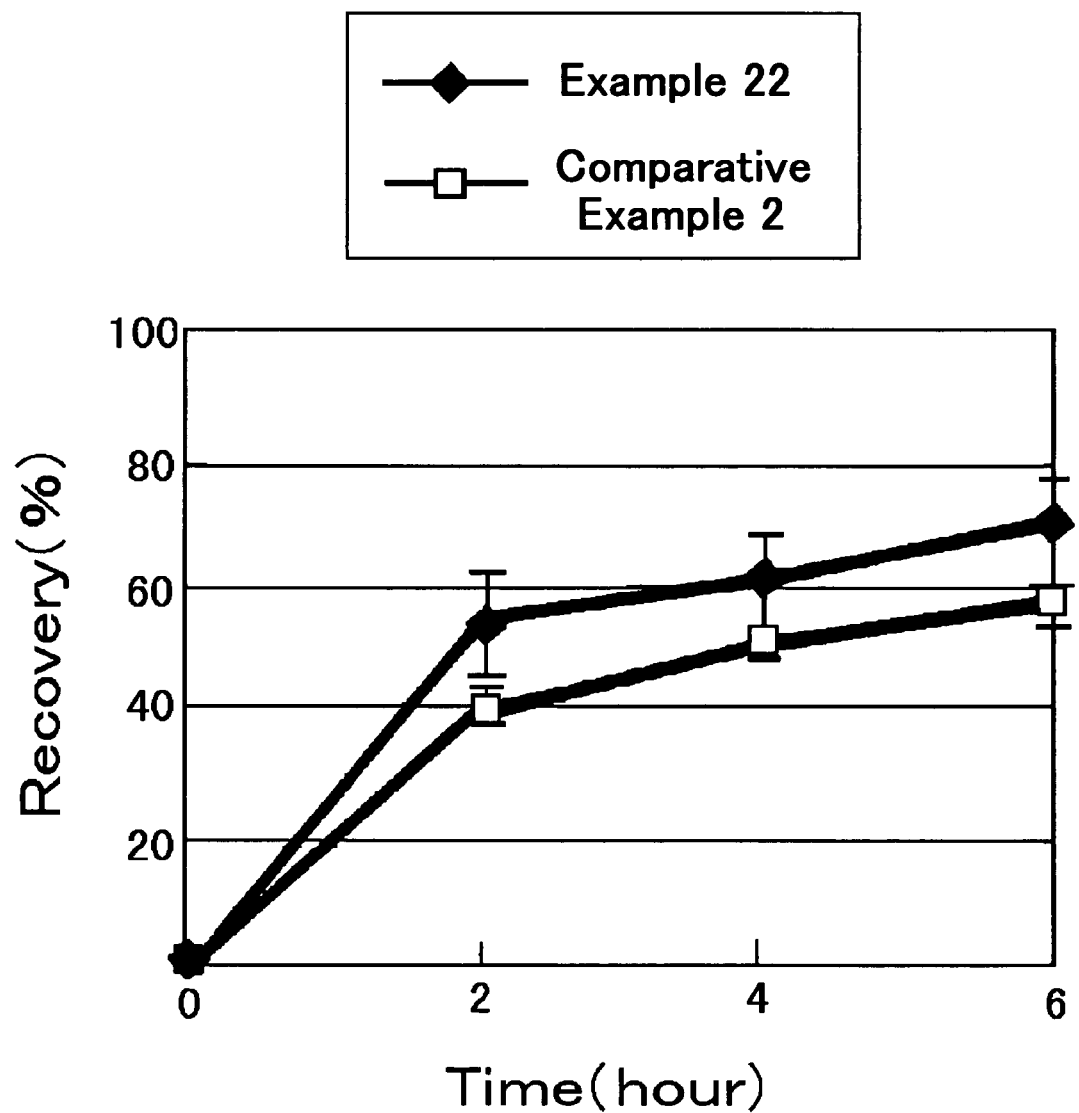
FIG. 7 is a view for comparing skin barrier function recovering effect between barium sulfate doped with zinc, and barium sulfate not doped with a metal.
Figure 8:
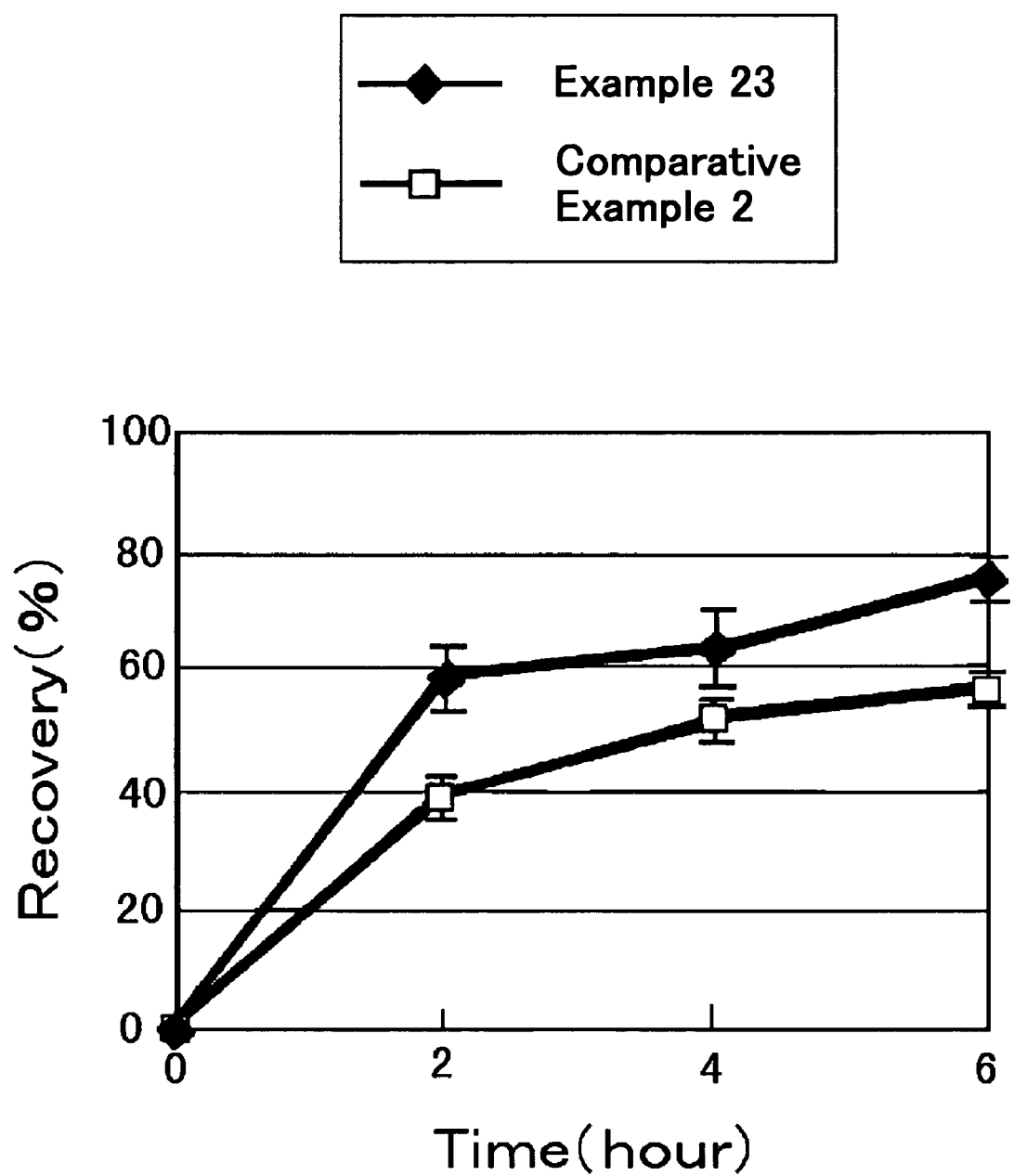
FIG. 8 is a view for comparing skin barrier function recovering effect between barium sulfate doped with sodium, and barium sulfate not doped with a metal.
Figure 9:
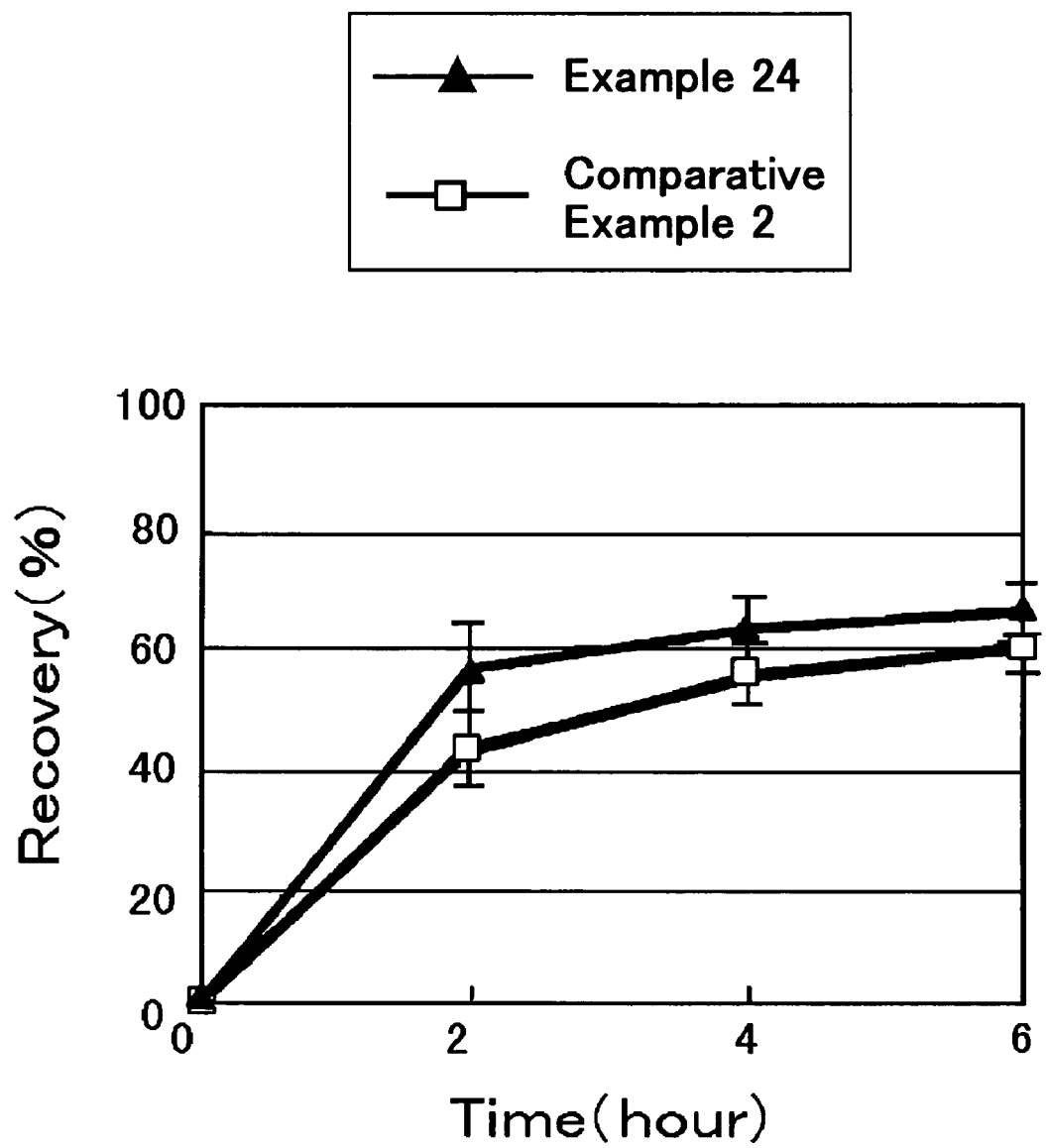
FIG. 9 is a view for comparing skin barrier function recovering effect between barium sulfate doped with lithium, and barium sulfate not doped with a metal.
Figure 10:
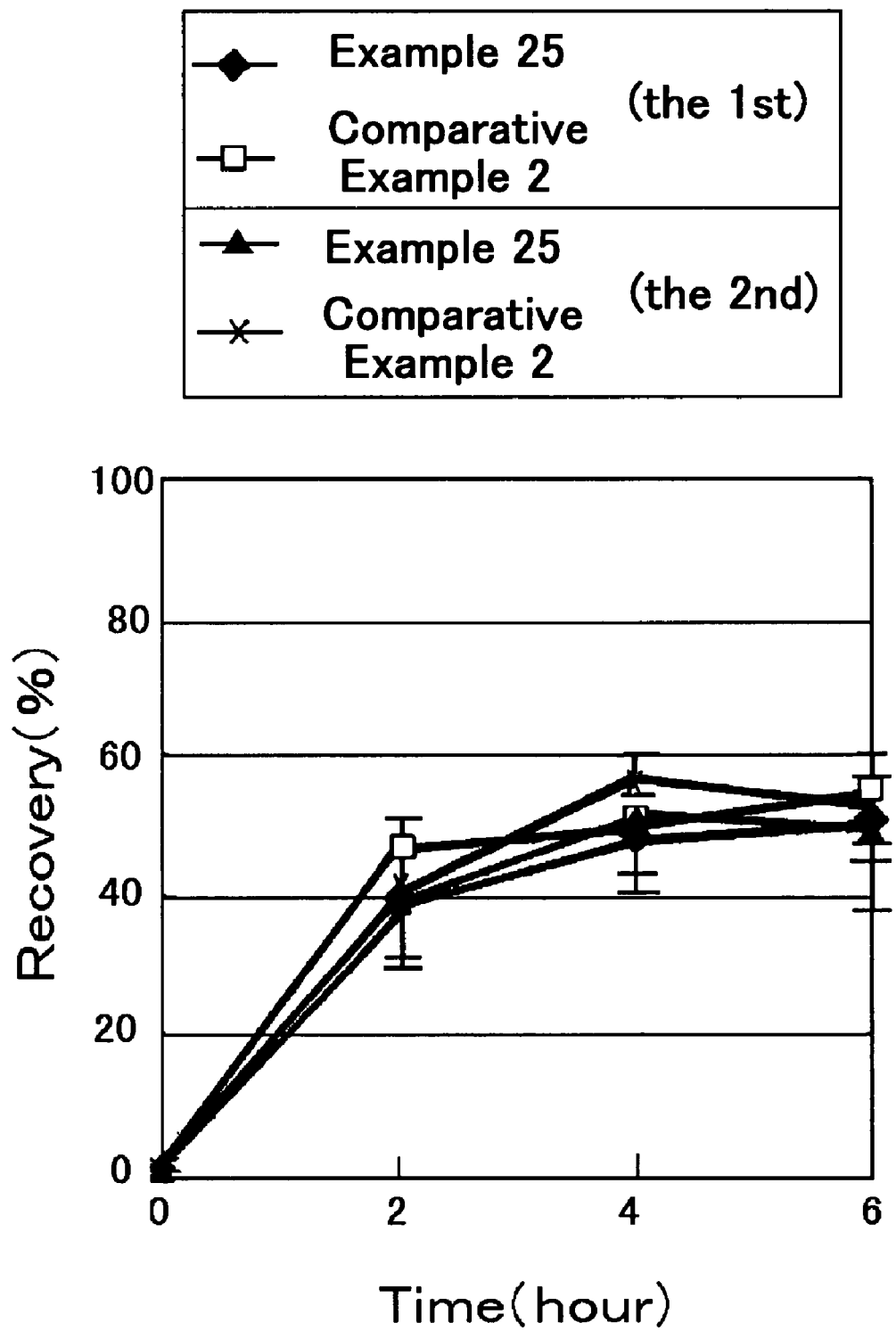
FIG. 10 is a view for comparing skin barrier function recovering effect between barium sulfate doped with calcium, and barium sulfate not doped with a metal.
Figure 11:
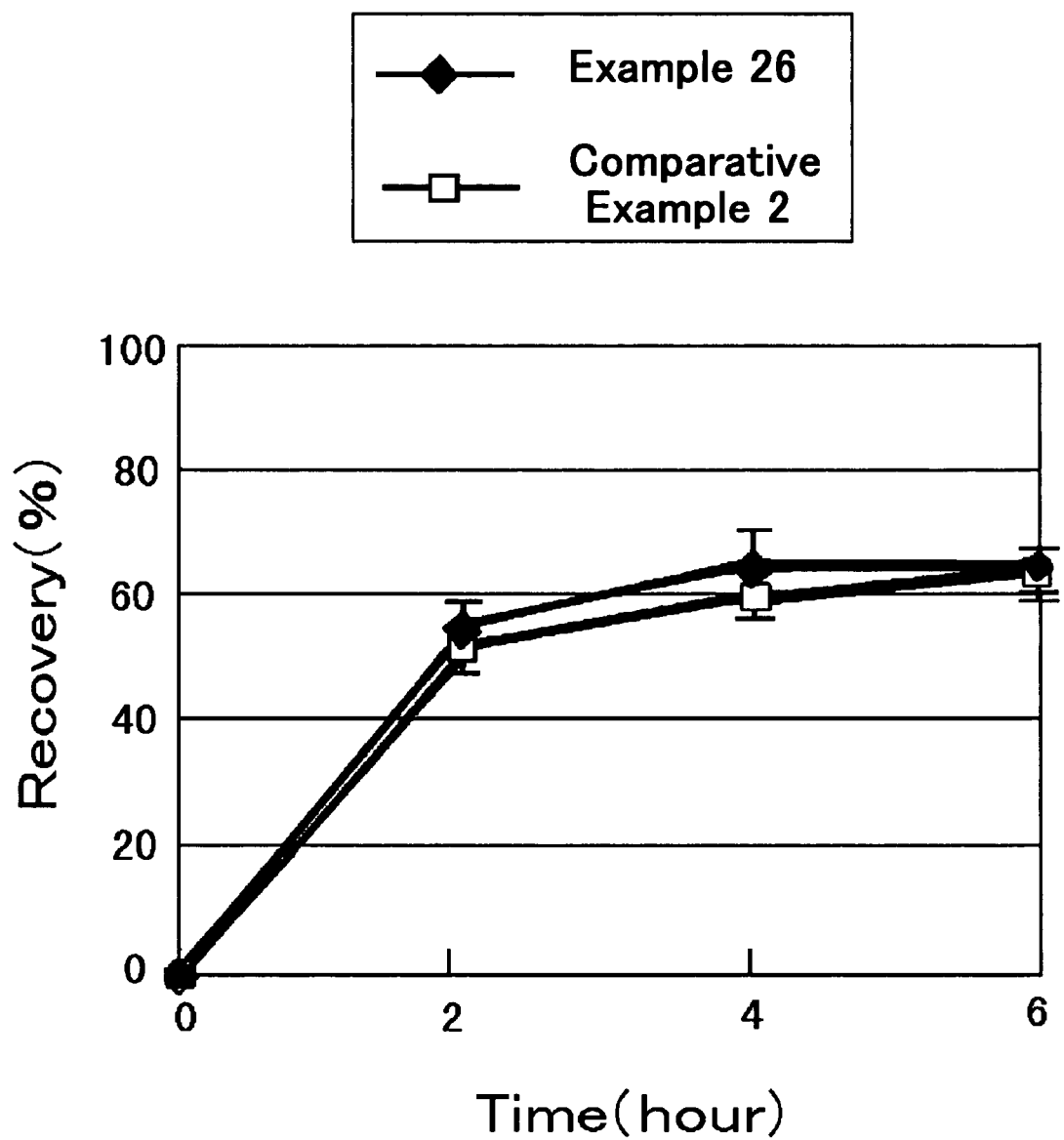
FIG. 11 is a view for comparing skin barrier function recovering effect between barium sulfate doped with aluminum, and barium sulfate not doped with a metal.
Figure 12:
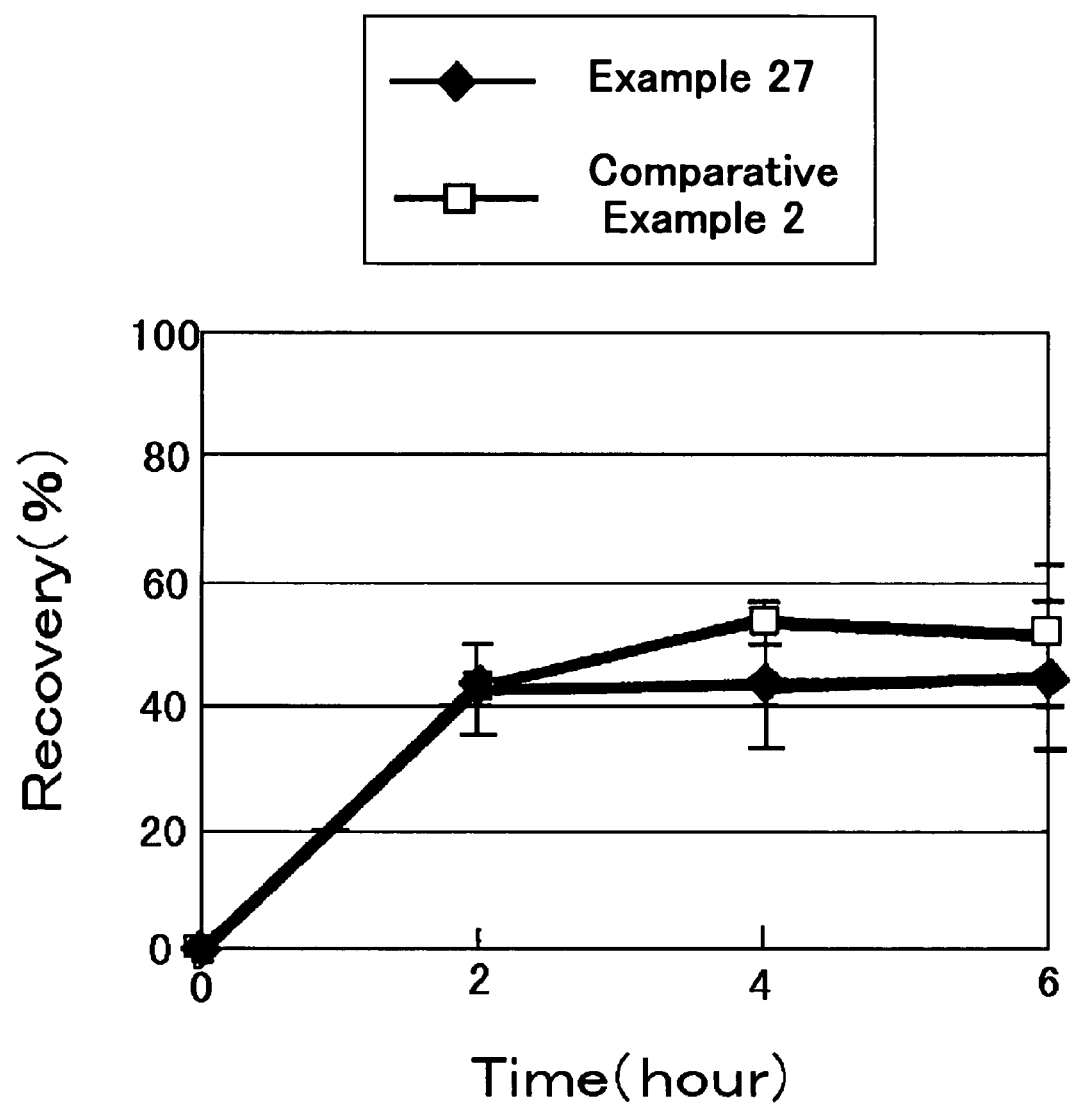
FIG. 12 is a view for comparing skin barrier function recovering effect between barium sulfate doped with magnesium, and barium sulfate not doped with a metal.
Figure 13:
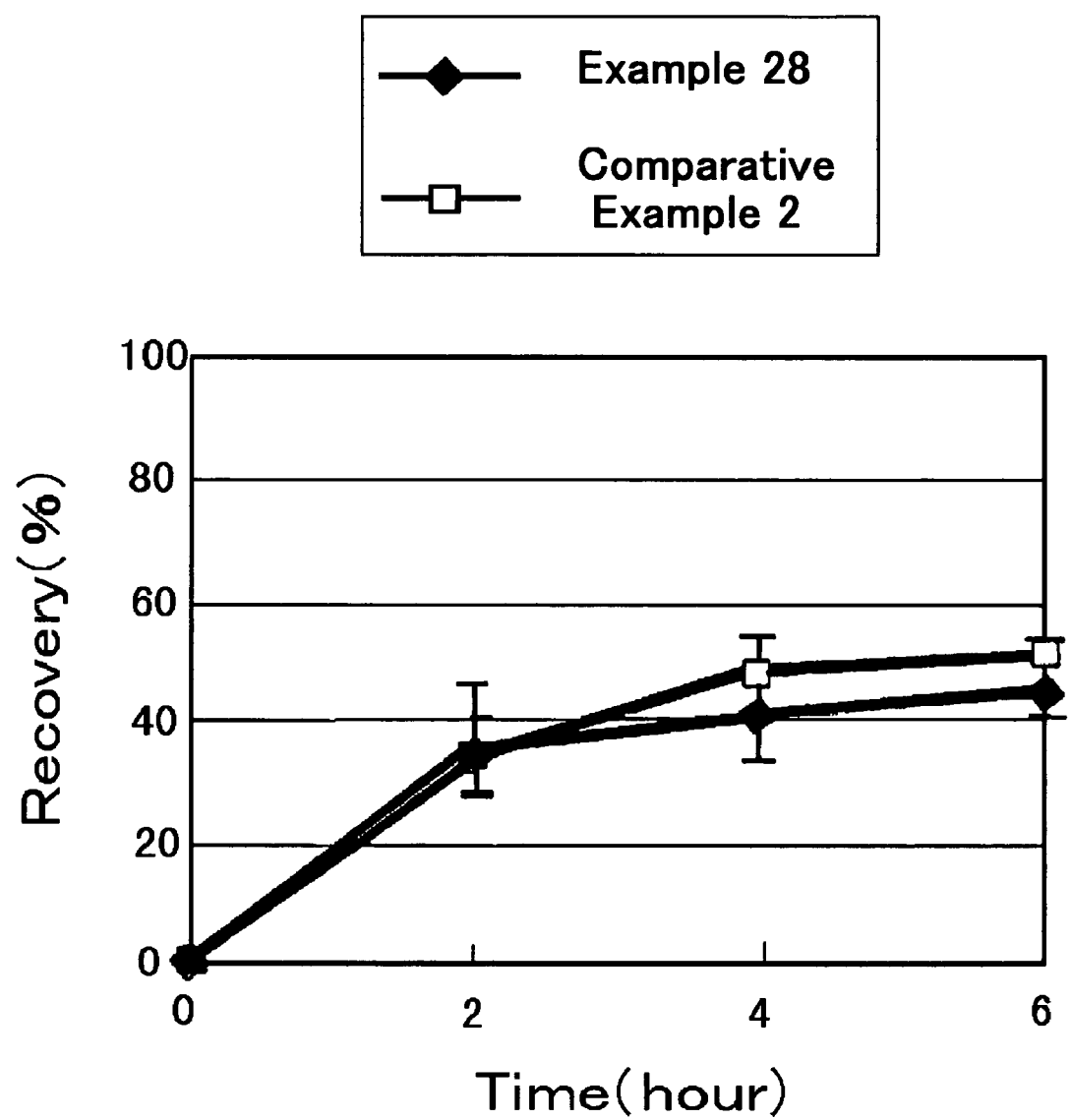
FIG. 13 is a view for comparing skin barrier function recovering effect between barium sulfate doped with iron, and barium sulfate not doped with a metal.

Two kinds of foundations of two utilities having the formulations shown in Table 5 were prepared, and were continuously coated on a human face for 8 hours or longer in the daytime for 2 weeks. A transdermal evaporating water level (TEWL) on a human face was measured with a water evaporation amount measuring apparatus (Meeco) before sample application and after continuous application for 2 weeks, and this was compared with the case of non-treatment. It can be said that as a TEWL value is lower, skin barrier function is recovered. Results are shown in FIG. 6 (n=9).

TABLE 5

| | Blending example | |
|---|---|---|
| | 4 | 5 |
| (1)Metal soap treated talc | residue | residue |
| (2)Silicone treated talc | 1.5 | 1.5 |
| (3)Silicone treated mica | 8 | 8 |
| (4)Silicone treated sericite | 30 | 30 |

TABLE 5-continued

| | Blending example | |
|---|---|---|
| | 4 | 5 |
| (5)Silicone treated synthesis mica | 4 | 4 |
| (6)Insoluble powder of Example 7 | 15 | 0 |
| (7)Silicone treated titanium oxide | 8 | 8 |
| (8)Silicone treated iron oxide | 2.7 | 2.7 |
| (9)Spherical alkyl polyacrylate resin powder | 6 | 6 |
| (10)Spherical alkyl polyacrylate resin fine powder coating mica | 7 | 7 |
| (11)Dimethylpolysiloxane | 5 | 5 |
| (12)Glycerol triisooctanoate | 3 | 3 |
| (13)2-Ethylhexyl para-methoxy-cinnamate | 3 | 3 |
| (14)Sorbitan sesuquiisostearate | 1 | 1 |
| (15)Antiseptics | proper quantity | proper quantity |
| (16)Antioxidant | proper quantity | proper quantity |
| (17)Perfume | proper quantity | proper quantity |

Ingredients (1) to (10) were mixed and ground, and heated and melted (11) to (17) were added thereto to stir and mix them, followed by further grinding treatment, which was molded under a pressure.

When Blending example 5 in which the insoluble powder of the present invention is not blended was coated, improvement in TEWL value is not observed, while when Blending example 4 in which 15% by weight of the insoluble powder of the present invention is blended was coated, a TEWL value was dramatically decreased from about 120 to about 60, and it was seen that skin barrier function was improved.

Therefore, it was confirmed that the insoluble powder of the present invention has skin barrier function recovering effect also in a human.

Then, in order to compare skin barrier function recovering effect between metal-doped type barium sulfate and barium sulfate not doped with a metal (Comparative example 2) in Table 6, the following experiment was performed. A skin barrier function recovery rate was calculated as described above. Results are shown in FIGS. 7 to 13.

TABLE 6

| | Kinds of insoluble powders | Doping element | Content by % |
|---|---|---|---|
| Example 22 | Zn doped barium sulfate | Zinc | 0.170% |
| Example 23 | Na doped barium sulfate | Sodium | 0.013% |
| Example 24 | Li doped barium sulfate | Lithium | <0.001% |
| Example 25 | Ca doped barium sulfate | Calcium | 0.074% |
| Example 26 | Al doped barium sulfate | Aluminum | 0.004% |
| Example 27 | Mg doped barium sulfate | Magnesium | 0.003% |
| Example 28 | Fe doped barium sulfate | Iron | 0.200% |
| Comparative 2 | Barium sulfate | — | — |

It was confirmed that, in the case where a powder of barium sulfate doped with Zn, Na or Li is used (Examples 22 to 24), skin barrier recovery is promoted as compared with the case where a powder of non-doped barium sulfate is used (Comparative example 2). In addition, in the case where a powder of barium sulfate doped with Ca or Al is used (Examples 25 and 26), there was no influence on skin barrier recovery. On the other hand, in the case where a powder of barium sulfate doped with Mg or Fe is used (Examples 27 and 28), it was confirmed that skin barrier recovery was conversely delayed.

Thereby, it was confirmed that a powder of barium sulfate doped with Zn, Li or Na has specifically excellent skin roughening improving effect as compared with barium sulfate not doped with a metal.

Skin Roughening Preventing and Improving Effect

The thickness of a skin of a hairless mouse receiving no damage was measured (Control example 2).

The whole back of a hairless mouse under drying was repeatedly wiped with acetone, giving damage.

20 mg of each powder of barium sulfate doped with a metal shown in Examples 22 and 28 in Table 6 was suspended in 100 to 200 μL of ion-exchanged water to prepare a suspension. The suspension was added dropwise to a 2 cm square of a filter placed on a plastic wrap to wet it. This was coated on a back of a hairless mouse after the aforementioned skin barrier destruction treatment for 10 minutes so that the added dropwise surface was contacted with the back, and peeled.

Figure 14:
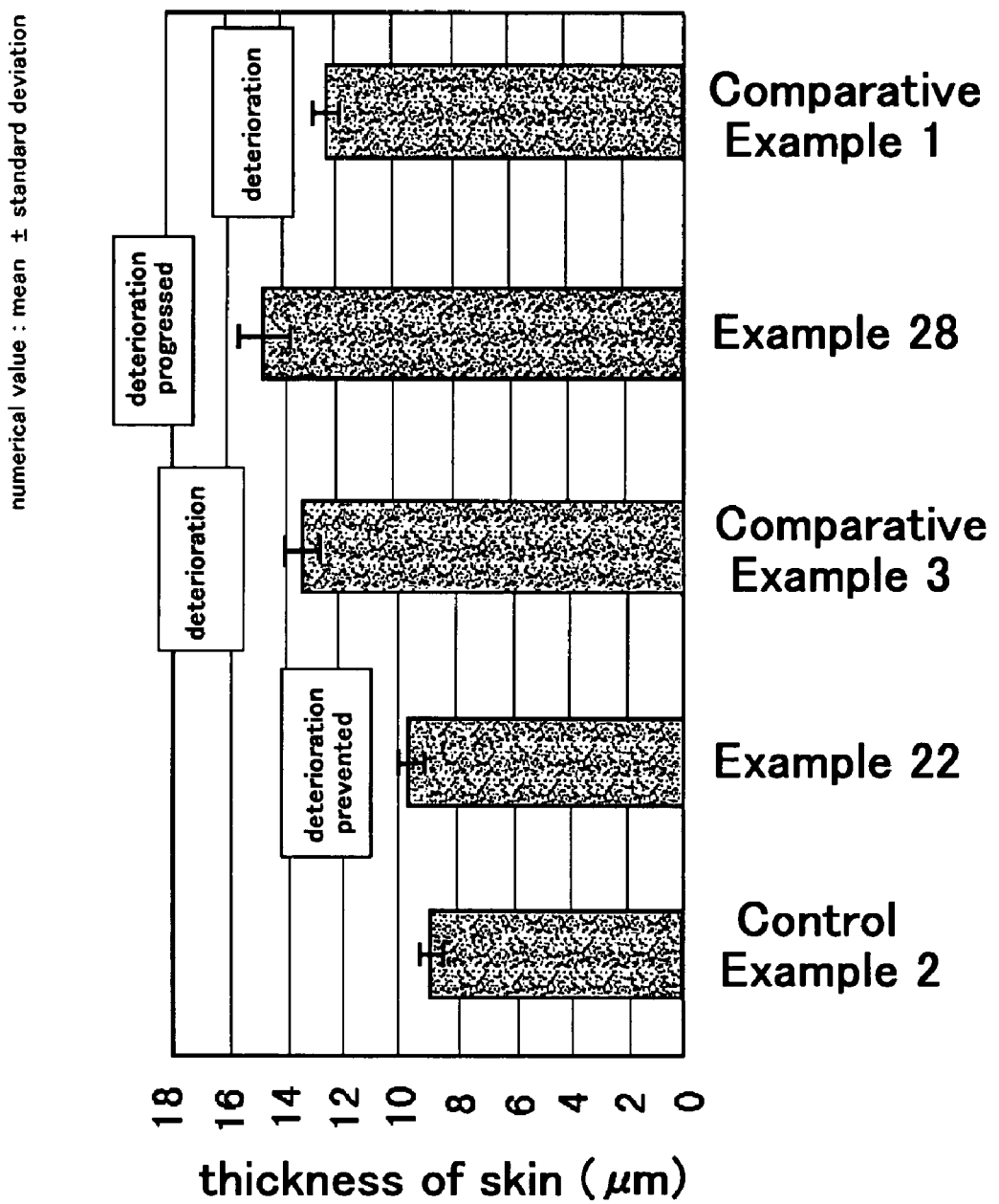
FIG. 14 is a view for comparing epidermis proliferating property abnormality preventing effect between barium sulfate doped with zinc, and barium sulfate doped with iron.

This was placed as it was under drying, thickness of a skin on a back of a hairless mouse after 2 days was measured, and was compared with thickness of a skin of a place not coated with a sample. When thickness of a skin is increased, it is determined that epidermis proliferating property abnormality occurred, and skin roughening occurred. Results are shown in FIG. 14.

It was confirmed that, at a place using a powder of barium sulfate doped with Fe of Example 28, epidermis proliferating property abnormality further progressed as compared with a place not coated with a sample (Comparative example 4), while at a place using a powder of barium sulfate doped with Zn of Example 22, epidermis proliferating property abnormality is prevented as compared with a place not coated with a sample (Comparative example 3). In addition, on appearance, falling was remarkably observed in Example 28, while no falling was recognized in Example 22. Thereby, it was confirmed that a powder of barium sulfate doped with Zn has excellent skin roughening preventing and improving effect.

| Embodiment 1 Barium sulfate | |
|---|---|
| Average primary particle diameter: | 3 to 10 μm |
| Aspect ratio: | 3 to 20 |
| Zeta-potential: | −2.31 |

(Preparation Process)

500 mL of 80 mmol/L aqueous barium chloride solution and 1000 mL of ion-exchanged water were stirred to mix in a 300 mL round bottom separable flask. After the liquid temperature was adjusted to 100° C., 500 mL of 80 mmol/L-aqueous sodium sulfate solution was added dropwise with stirring. Immediately, white barium sulfate was produced and precipitated, and the reaction solution became the suspended state. After addition of an aqueous solution of sodium sulfate, a reaction was carried out for 1 hour. After completion of the reaction, the reaction solution was cooled to room temperature, the resulting solid product was precipitated, filtered and washed with water to remove a salt, followed by drying at 120° C. for 12 hours. Then, the solid product was subjected to grinding treatment (grinding treatment was carried out for 5 minutes using a small size-grinding machine) to obtain a white powder.

Figure 15:
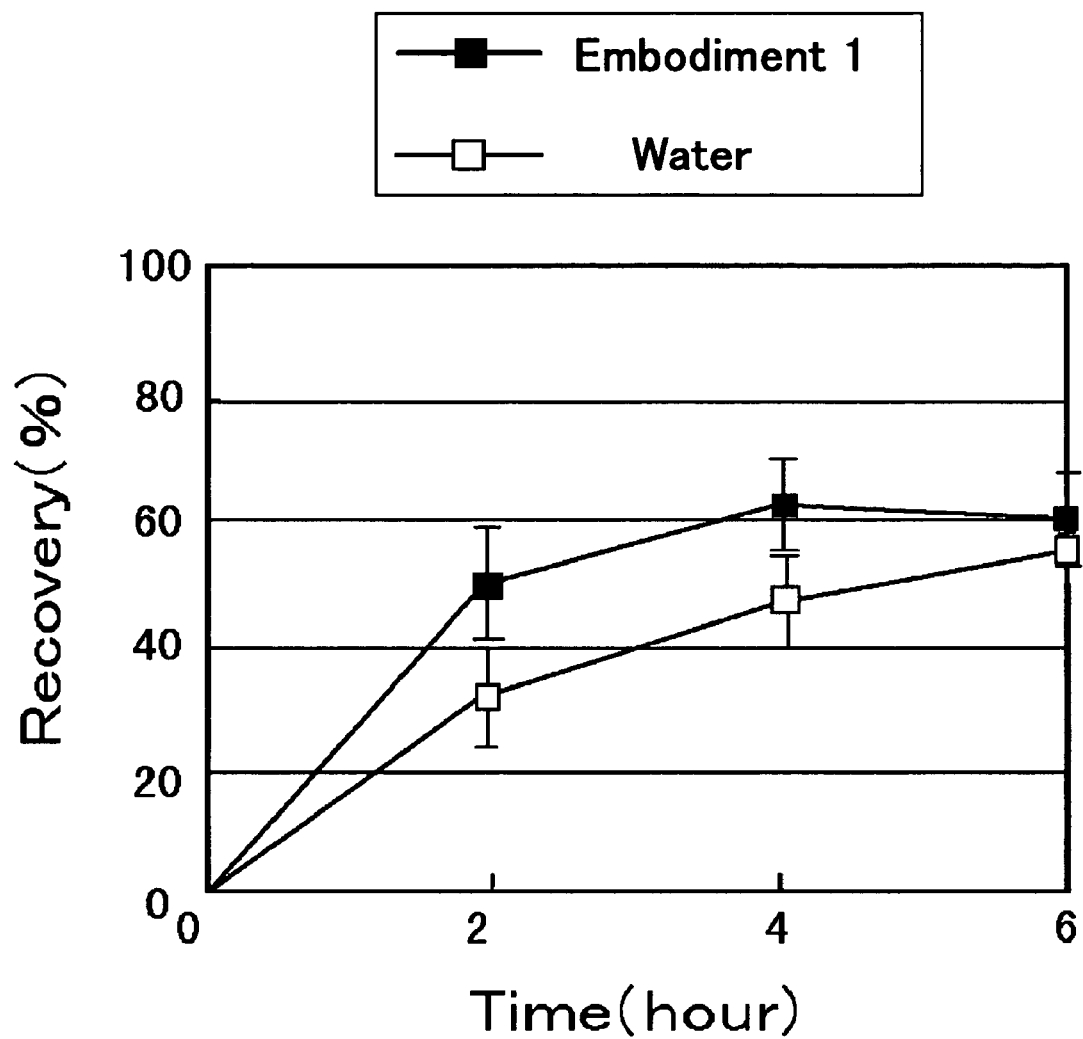
FIG. 15 is a view showing skin barrier recovering effect of the insoluble powder of embodiment 1.

According to the aforementioned method of measuring skin barrier function recovery rate, a skin barrier function recovery rate was measured, and the results are shown in FIG. 15.

| Embodiment 2 Barium sulfate | |
|---|---|
| Average primary particle diameter: | 3-15 μm, |
| Aspect ratio: | 3-30, |
| Zeta-potential: | −3.31 |

(Preparation Process)

500 mL of 60 mmol/L aqueous barium chloride solution and 1000 mL of ion-exchanged water were stirred to mix in a 300 mL round bottom separable flask. After the liquid temperature was adjusted to 100° C., 500 mL of 60 mmol/L-aqueous sodium sulfate solution was added dropwise with stirring. Immediately, white barium sulfate was produced and precipitated, and the reaction solution became the suspended state. After addition of an aqueous solution of sodium sulfate, a reaction was carried out for 1 hour. After completion of the reaction, the reaction solution was cooled to room temperature, the resulting solid product was precipitated, filtered and washed with water to remove a salt, followed by drying at 120° C. for 12 hours. Then, the solid product was subjected to grinding treatment (grinding treatment was carried out for 5 minutes using a small size-grinding machine) to obtain a white powder.

Figure 16:
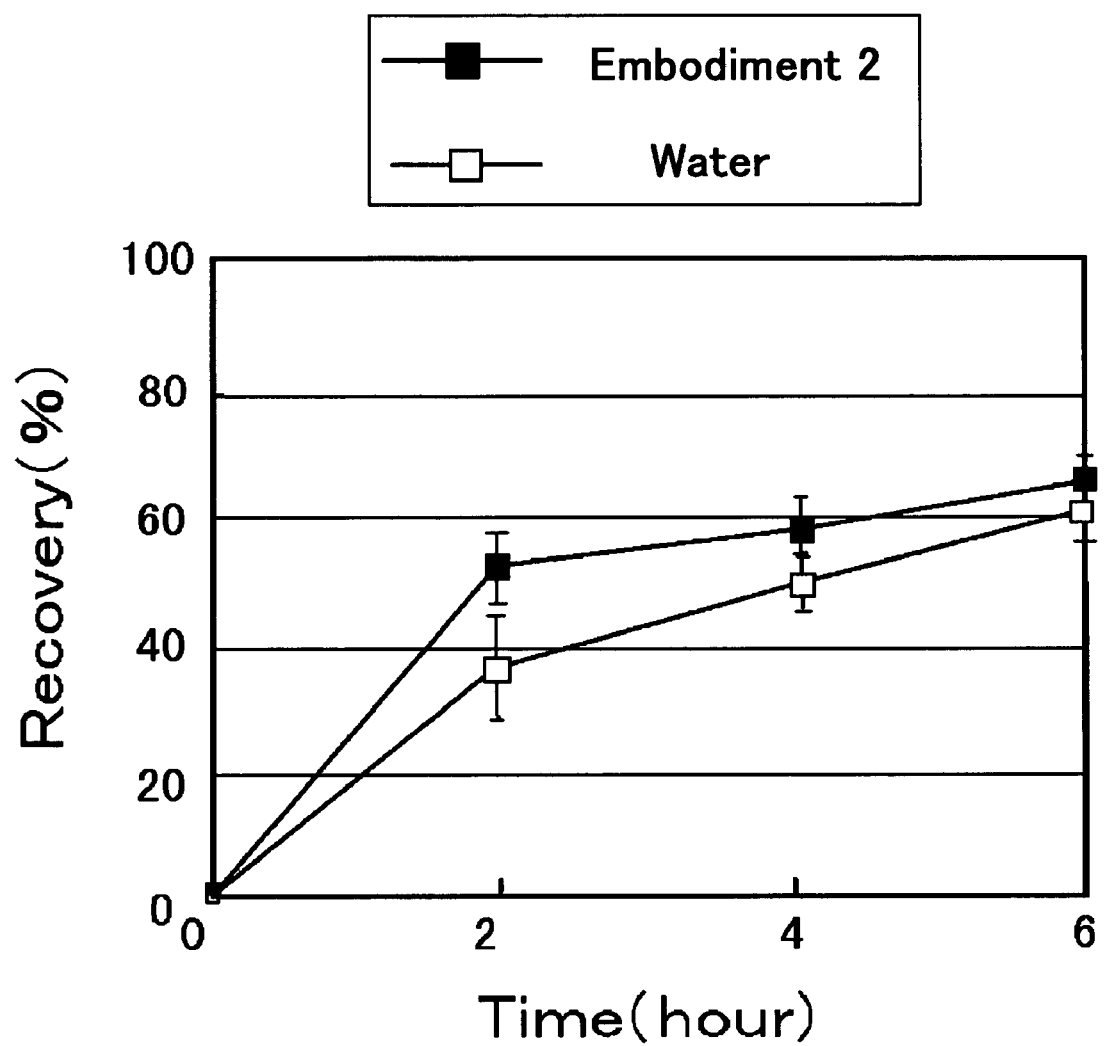
FIG. 16 is a view showing skin barrier recovering effect of the insoluble powder of embodiment 2.

According to the aforementioned method of measuring skin barrier function recovery rate, a skin barrier function recovery rate was measured, and the results are shown in FIG. 16.

| Embodiment 3 Barium sulfate | |
|---|---|
| Average primary particle diameter: | 3-20 μm, |
| Aspect ratio: | 3-40, |
| Zeta-potential: | −3.69 |

(Preparation Process)

500 mL of 40 mmol/L aqueous barium chloride solution and 1000 mL of ion-exchanged water were stirred to mix in a 300 mL round bottom separable flask. After the liquid temperature was adjusted to 100° C., 500 mL of 40 mmol/L-aqueous sodium sulfate solution was added dropwise with stirring. Immediately, white barium sulfate was produced and precipitated, and the reaction solution became the suspended state. After addition of an aqueous solution of sodium sulfate, a reaction was carried out for 1 hour. After completion of the reaction, the reaction solution was cooled to room temperature, the resulting solid product was precipitated, filtered and washed with water to remove a salt, followed by drying at 120° C. for 12 hours. Then, the solid product was subjected to grinding treatment (grinding treatment was carried out for 5 minutes using a small size-grinding machine) to obtain a white powder.

Figure 17:
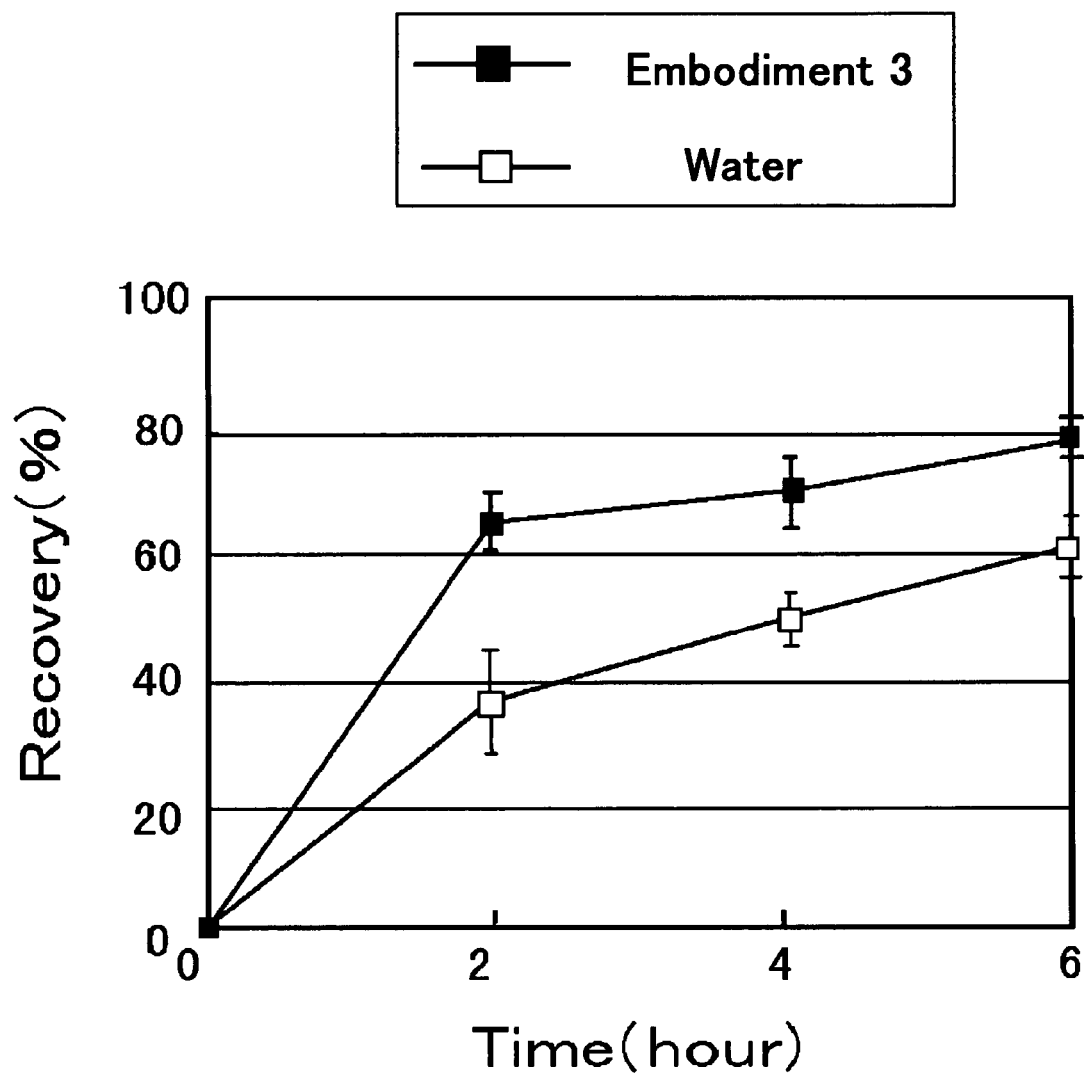
FIG. 17 is a view showing skin barrier recovering effect of the insoluble powder of embodiment 3.

According to the aforementioned method of measuring skin barrier function recovery rate, a skin barrier function recovery rate was measured, and the results are shown in FIG. 17.

| Embodiment 4 Lithium dope barium sulfate | |
|---|---|
| Average primary particle diameter: | 5-20 μm, |
| Aspect ratio: | 5-100, |
| Zeta-potential: | −2.34 |

(Preparation Process)

500 mL of 60 mmol/L/aqueous barium chloride solution, 500 mL of 60 mmol/L/aqueous lithium chloride solution and 1000 mL of ion-exchanged water were stirred to mix in a 300 mL round bottom separable flask. After the liquid temperature was adjusted to 100° C., 500 mL of 60 mmol/L-aqueous sodium sulfate solution was added dropwise with stirring. Immediately, white barium sulfate was produced and precipitated, and the reaction solution became the suspended state. After addition of an aqueous solution of sodium sulfate, a reaction was carried out for 1 hour. After completion of the reaction, the reaction solution was cooled to room temperature, the resulting solid product was precipitated, filtered and washed with water to remove a salt, followed by drying at 120° C. for 12 hours. Then, the solid product was subjected to grinding treatment (grinding treatment was carried out for 5 minutes using a small size-grinding machine) to obtain a white powder.

Figure 18:
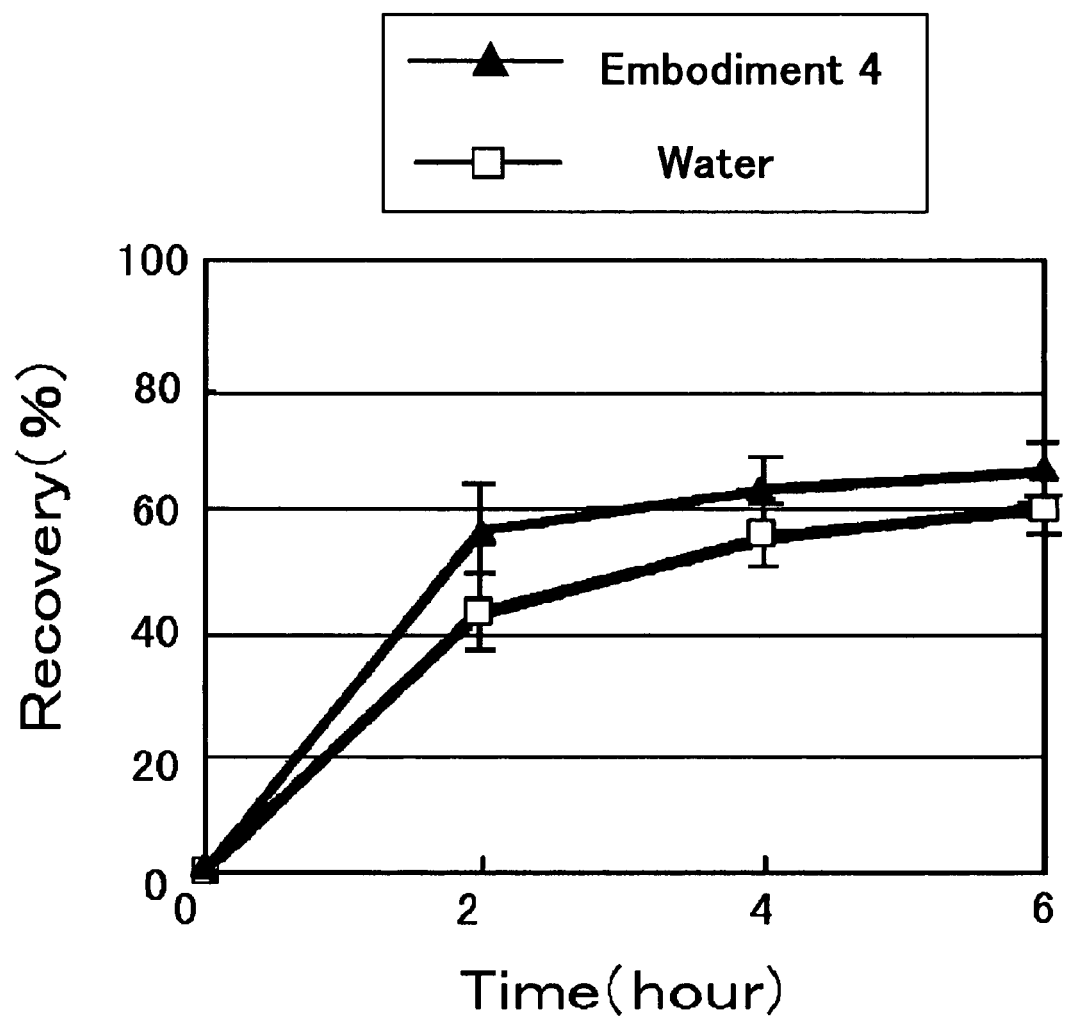
FIG. 18 is a view showing skin barrier recovering effect of the insoluble powder of embodiment 4.

According to the aforementioned method of measuring skin barrier function recovery rate, a skin barrier function recovery rate was measured, and the results are shown in FIG. 18.

| Embodiment 5 Sodium dope barium sulfate | |
|---|---|
| Average primary particle diameter: | 30-50 μm, |
| Aspect ratio: | 30-250, |
| Zeta-potential: | −1.71 |

(Preparation Process)

500 mL of 60 mmol/L/aqueous barium chloride solution, 500 mL of 60 mmol/L/aqueous sodium chloride solution and 1000 mL of ion-exchanged water were stirred to mix in a 300 mL round bottom separable flask. After the liquid temperature was adjusted to 100° C., 500 mL of 60 mmol/L-aqueous sodium sulfate solution was added dropwise with stirring. Immediately, white barium sulfate was produced and precipitated, and the reaction solution became the suspended state. After addition of an aqueous solution of sodium sulfate, a reaction was carried out for 1 hour. After completion of the reaction, the reaction solution was cooled to room temperature, the resulting solid product was precipitated, filtered and washed with water to remove a salt, followed by drying at 120° C. for 12 hours. Then, the solid product was subjected to grinding treatment (grinding treatment was carried out for 5 minutes using a small size-grinding machine) to obtain a white powder.

Figure 19:
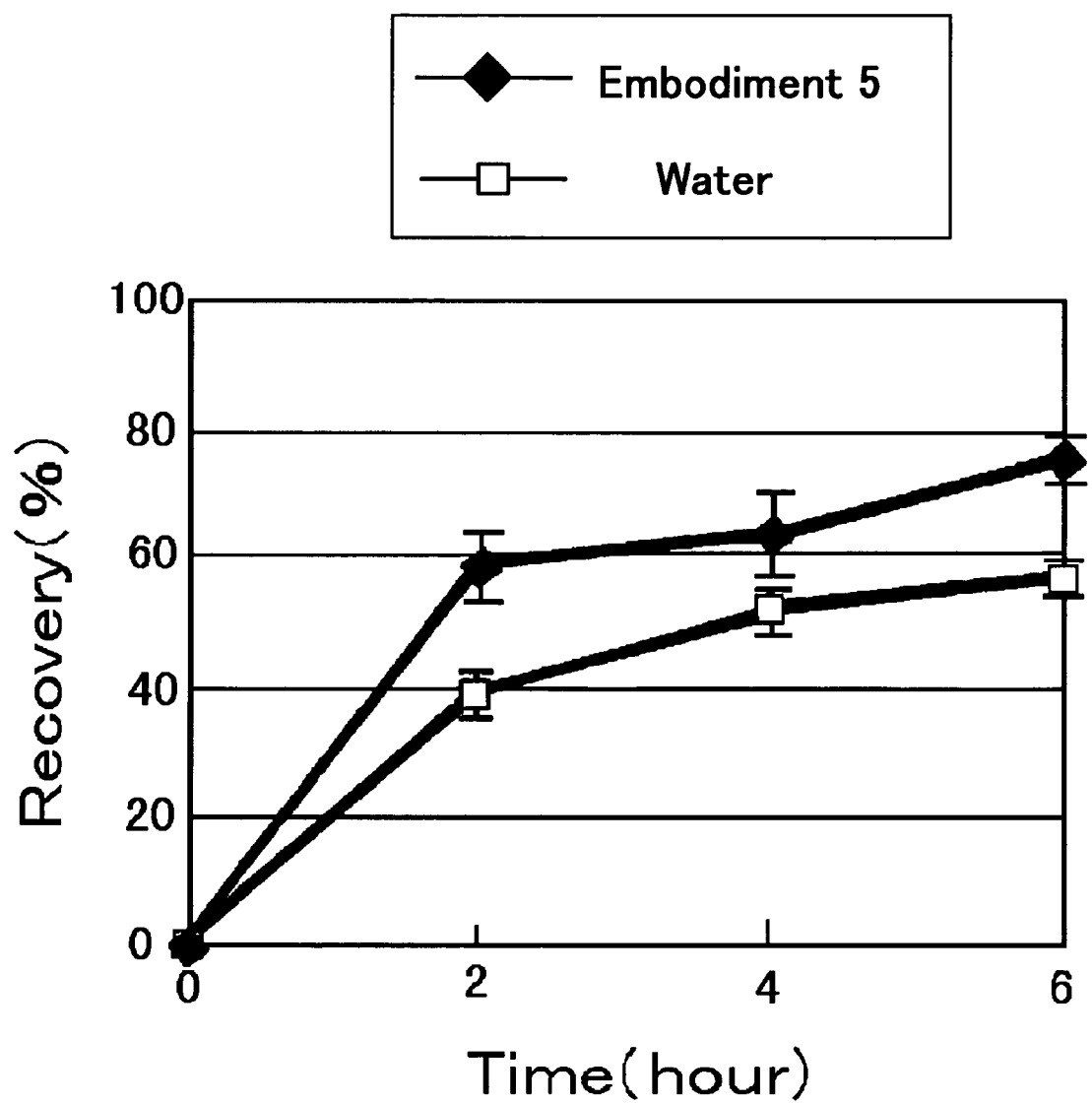
FIG. 19 is a view showing skin barrier recovering effect of the insoluble powder of embodiment 5.

According to the aforementioned method of measuring skin barrier function recovery rate, a skin barrier function recovery rate was measured, and the results are shown in FIG. 19.

Embodiment 6 Zinc Dope Barium Sulfate (Preparation Process)

500 mL of 0.06 mol/L/aqueous barium chloride solution, 500 mL of 0.06 mol/L/aqueous zinc chloride solution and 1 L of ion-exchanged water were stirred to mix in a 3 L round bottom separable flask. After the liquid temperature was adjusted to 100° C., 500 mL of 0.06 mol/L-aqueous sodium sulfate solution was added dropwise with stirring. Immediately, white barium sulfate was produced and precipitated, and the reaction solution became the suspended state. After addition of an aqueous solution of sodium sulfate, a reaction was carried out for 1 hour. After completion of the reaction, the reaction solution was cooled to room temperature, the resulting solid product was precipitated, filtered and washed with water to remove a salt, followed by drying at 120° C. for 12 hours.

Figure 20:
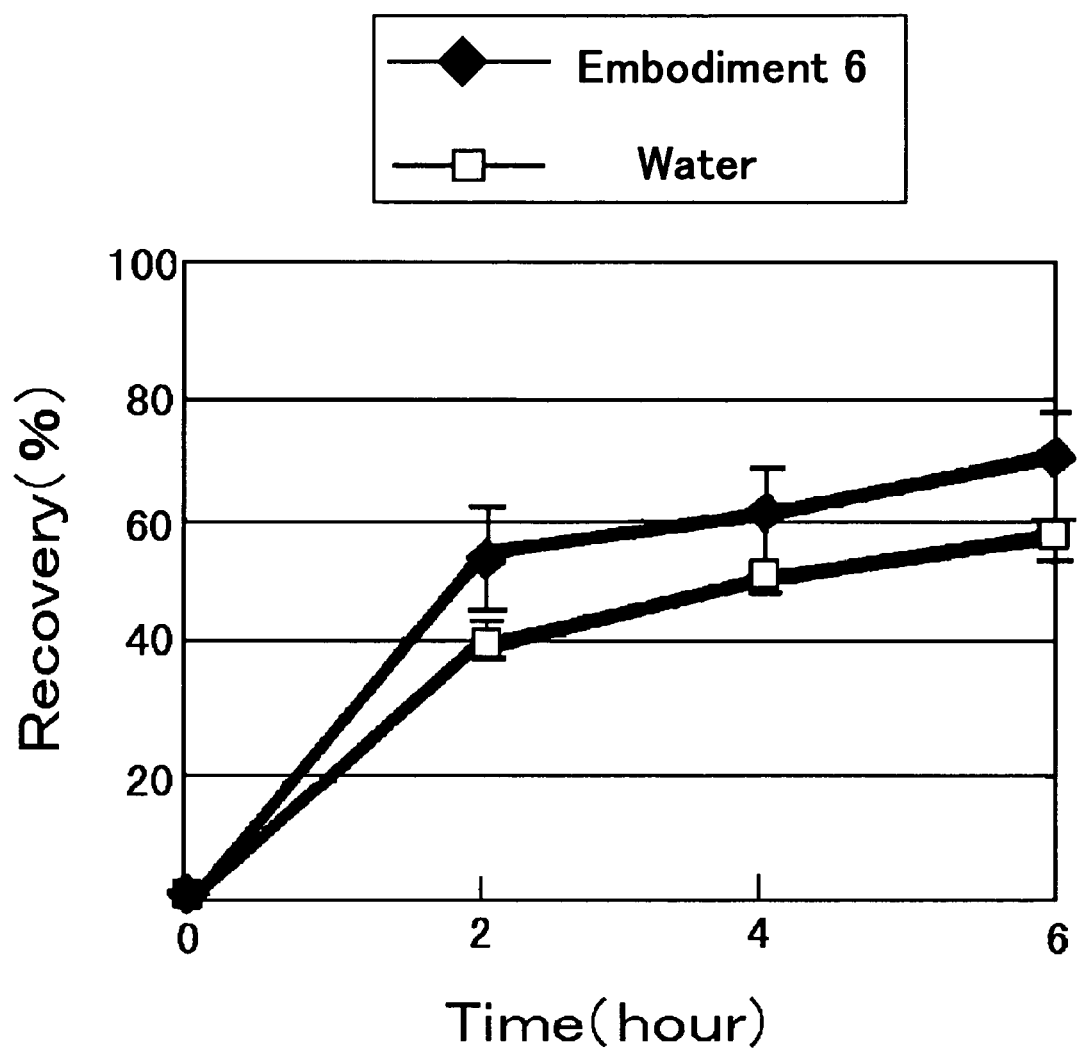
FIG. 20 is a view showing skin barrier recovering effect of the insoluble powder of embodiment 6.

According to the aforementioned method of measuring skin barrier function recovery rate, a skin barrier function recovery rate was measured, and the results are shown in FIG. 20.

| Embodiment 7 Solid powdery foundation | |
|---|---|
| (prescription) | Wt % |
| (1) Silicone treated sericite | 15 |
| (2) Silicone treated mica | 20 |
| (3) Silicone treated synthesis mica | 10 |
| (4) Silicone treated talc | remainder |
| (5) Network type silicone resin covering organo polysiloxane elastomer spherical powder | 3 |
| (6) Methyl siloxane network polymer spherical powder | 4 |
| (7) Barium sulfate (Average primary particle size: 10 μm, aspect ratio: 10, zeta-potential: −0.3 mV) | 10 |
| (8) Zinc myristate | 2 |
| (9) Powdery hydrocarbon wax | 3 |
| (10) Silicone treated titanium oxide | 10 |
| (11) Silicone treated iron oxide | 4 |
| (12) Silicone treated zinc oxide | 5 |
| (13) Squalane | 3 |
| (14) Dimethylpolysiloxane | 4 |
| (15) Paramethoxy cinnamate 2-ethylhexyl | 3 |
| (16) Polyoxyethylene polyalkyl modified silicone | 1 |
| (17) Sorbitan sesqui isostearate | 1 |
| (18) Antiseptics | proper quantity |
| (19) Anti oxidant | proper quantity |
| (20) Perfume | proper quantity |

(Process)

Respective ingredients of 1 to 12 were mixed and ground, respective ingredients of 13 to 20 were added to mix thereto with stirring and mix them, this was further ground, and was molded in a container to obtain a solid powdery foundation.

| Embodiment 8 Baby powder | |
|---|---|
| (prescription) | wt % |
| (1) Talc | remainder |
| (2) Synthesis mica | 12 |
| (3) Magnesium stearate | 4 |
| (4) Zinc white | 3 |
| (5) Barium sulfate (Average primary particle size: 20 μm, aspect ratio: 40, zeta-potential: −3.7 mV) | 20 |
| (6) Perfume | proper quantity |

(Process)

Respective ingredients 1 to 5 were stirred to mix, 6 was sprayed thereto, and this was mixed and subjected to grinding treatment to obtain a baby powder.

Embodiment 9 White powder

| (prescription) | wt % |
|---|---|
| (1) Talc | remainder |
| (2) Mica | 12 |
| (3) Sericite | 8 |
| (4) Spherical methyl siloxane network polymer powder | 3 |
| (5) Boron nitride | 4 |
| (6) Barium sulfate | 40 |
| (Average primary particle size: 20 μm, aspect ratio: 40, zeta-potential: −3.7 mV) | |
| (7) Iron oxide | 2 |
| (8) Ultramarineblue covering mica titanium | 1 |
| (9) N-acylated lysine | 2 |
| (10) Zinc myristate | 3 |
| (11) Powdery synthesis polyethylene wax | 1 |
| (12) Gycerin triisooctanoate | 3 |
| (13) Liquid paraffin | 2 |
| (14) Sorbitan sesqui isostearate | 0.5 |
| (15) Antiseptics | proper quantity |
| (16) Perfume | proper quantity |

(Process)

Respective ingredients of 1 to 11 were stirred to mix, uniformly mixed 12 to 16 were added thereto to mix and grind them, and this was molded into an intermediate dish to obtain a white powder.

Embodiment 10 O/W type emulsion cosmetic

| (prescription) | Wt % |
|---|---|
| (1) Purified water | remainder |
| (2) Propylene glycol | 4 |
| (3) Glycerol | 2 |
| (4) Sodium methaphosphate | proper quantity |
| (5) Bentonite | 2 |
| (6) Potassium hydroxide | 0.4 |
| (7) Palmitic acid | 1.2 |
| (8) Isostearic acid | 1 |
| (9) Titanium oxide | 10 |
| (10) Iron oxide | proper quantity |
| (11) Spherical silica powder | 5 |
| (12) Barium sulfate | 8 |
| (Average primary particle size: 20 μm, aspect ratio: 7, zeta-potential: −0.3 mV) | |
| (13) Talc | 4 |
| (14) Mica | 2 |
| (15) Mica titanium | 1 |
| (16) Glycerin monostearate | 1 |
| (17) Polyoxyethylene sorbitan monostearate | 0.5 |
| (18) Cetyl alcohol | 0.4 |
| (19) Batyl alcohol | 0.5 |
| (20) Liquid paraffin | 5 |
| (21) Dimethylpolysiloxane | 5 |
| (22) Paramethoxy cinnamate acid 2-ethylhexyl | 3 |
| (23) Vaseline | 1 |
| (24) Antiseptics | proper quantity |
| (25) Perfume | proper quantity |

(Process)

1 to 5 were uniformly stirred to mix, 6 to 8 were added thereto to mix them, and mixed and ground 9 to 15 were added thereto to disperse them. To this were added heated and melted 16 to 25, and this was uniformly emulsified to obtain an oil in water-type emulsion cosmetic.

Embodiment 11 W/O type emulsion cosmetic

| (prescription) | Wt % |
|---|---|
| (1) Spherical polyurethane powder | 3 |
| (2) Silicone treated mica titanium | 2 |
| (3) Barium sulfate | 4 |
| (Average primary particle size: 30 μm, aspect ratio: 15, zeta-potential: −1.7 mV) | |
| (4) Silicone treated titanium oxide | 10 |
| (5) Silicone treated iron oxide | 4 |
| (6) Silicone treated talc | 2 |
| (7) Silicone treated baking mica | 3 |
| (8) Purified water | remainder |
| (9) Dipropylene glycol | 8 |
| (10) Decamethyl cyclopenta siloxane | 25 |
| (11) Dodevamethyl cyclohexa siloxane | 15 |
| (12) Dimethylpolysiloxane | 3 |
| (13) Silicone resin | 2 |
| (14) Polyether modified silicone | 1.5 |
| (15) Alkyl polyether modified silicone | 0.5 |
| (16) Isostearic acid | 1 |
| (17) Antioxidant | proper quantity |
| (18) Antiseptics | proper quantity |

(Process)

Respective ingredients 10 to 18 were uniformly mixed, mixed and ground respective ingredients 1 to 7 were added thereto to disperse them. Then, uniformly mixed and melted 8 to 9 were added to emulsify them, which was charged into a container to obtain a water in oil type emulsion cosmetic.

Embodiment 12 Eyes shadow

| (prescription) | Wt % |
|---|---|
| (1) Talc | remainder |
| (2) Sericite | 7 |
| (3) Mica | 15 |
| (4) Spherical polymethyl methacrylate powder | 3 |
| (5) Spherical styrene resin covering synthesis mica | 2 |
| (6) Iron oxide covering mica titanium | 4 |
| (7) Iron oxide | 1.5 |
| (8) Barium sulfate | 10 |
| (Average primary particle size: 20 μm, aspect ratio: 15, zeta-potential: −2.4 mV) | |
| (9) Squalane | 2 |
| (10) Dimethylpolysiloxane | 2 |
| (11) Sorbitan monooleate | 0.5 |
| (12) Antiseptics | proper quantity |
| (13) Perfume | proper quantity |

(Process)

Respective ingredients 1 to 8 were mixed and ground, mixed respective ingredients of 9 to 13 were added thereto to stir and mix them, and this was molded into an intermediate dish to obtain an eyes shadow.

Embodiment 13 Oily stick

| (prescription) | Wt % |
|---|---|
| (1) Carnauba wax | 1 |
| (2) Candelilla wax | 2 |
| (3) Ceresin | 10 |
| (4) Squalane | remainder |
| (5) Glycerin triisooctanoate | 9 |
| (6) Glycerin diisostearate | 13 |

-continued

Embodiment 13 Oily stick

| (prescription) | Wt % |
|---|---|
| (7) Dimethylpolysiloxane | 5 |
| (Viscosity: 90,000 mPa · s at 25° C.) | |
| (8) Dimethylpolysiloxane | 5 |
| (Viscosity: 1,000 mPa · s at 25° C.) | |
| (9) Silicone resin | 8 |
| (10) Hydroxy propyl-beta-cyclodextrin | 1 |
| (11) Macademian nut oil fatty acid cholesteryl | 3.5 |
| (12) Synthesis sodium silicate magnesium | 0.5 |
| (13) Hydrophobic silica | 0.5 |
| (14) Purified water | 2 |
| (15) Spherical silicone resin powder coating mica | 3 |
| (16) Spherical nylon powder | 4 |
| (17) Barium sulfate | 10 |
| (Average primary particle size: 40 μm, aspect ratio: 10, zeta-potential: −1.7 mV) | |
| (18) Coloring material | proper quantity |
| (19) Antiseptics | proper quantity |
| (20) Perfume | proper quantity |

(Process)

12 to 13 were dispersed into 11 heated to 60° C., and uniformly melted 10 and 14 were added thereto to sufficiently stir them. This was added to separately heated and melted 1 to 9 to sufficiently stir them, 15 to 20 were further added to disperse and stir them and, thereafter, this was charged into a container to obtain an oily stick.

Embodiment 14 Powdery foundation

| (prescription) | Wt % |
|---|---|
| Sericite | 8 |
| Synthesis mica | 5 |
| Talc | too 100 |
| Silica covering zinc oxide | 5 |
| Zinc-dope barium sulfate | 22 |
| Spherical nylon powder | 5 |
| Spherical silicone elastic powder | 15 |
| Titanium oxide | 12 |
| Ferric oxide | 0.8 |
| Yellow iron oxide | 2 |
| Black iron oxide | 0.1 |
| Dimethylpolysiloxane | 3 |
| Liquid paraffin | 5 |
| Vaseline | 5 |
| Sorbitan sesqui isostearate | 1 |
| Paraben | proper quantity |
| Anti-Oxidant | proper quantity |
| Perfume | proper quantity |

(Process)

The aforementioned all ingredients were ground and mixed with a bead medium mill for a constant time in an alcohol, the resulting slurry was charged into an intermediate dish container, and pressed while an alcohol was sucked, to prepare a powdery foundation.

Embodiment 15 Powdery foundation

| (prescription) | Wt % |
|---|---|
| Mica | 23 |
| Baking sericite | 15 |
| Lecithin treated zinc-dope barium sulfate | 10 |

Embodiment 15 Powdery foundation

| (prescription) | Wt % |
|---|---|
| Zinc-dope talc | too 100 |
| Spherical silicone powder | 5 |
| Spherical silicone elastic powder | 10 |
| Titanium oxide | 12 |
| Ferric oxide | 0.8 |
| Yellow iron oxide | 2 |
| Black iron oxide | 0.1 |
| Dimethylpolysiloxane | 4 |
| Liquid paraffin | 6 |
| Vaseline | 5 |
| Sorbitan sesqui isostearate | 1 |
| Paraben | proper quantity |
| Oxidation inhibitor | proper quantity |
| Perfume | proper quantity |

(Process)

The aforementioned all ingredients were ground and mixed with a bead medium mill for a constant time in an alcohol, the resulting slurry was charged into an intermediate dish container, and pressed while an alcohol was sucked, to prepare a powdery foundation.

Embodiment 16 Powdery foundation

| (prescription) | wt % |
|---|---|
| Silicone treated sericite | 18 |
| Silicone treated synthesis mica | 12 |
| Silicone treated talc | too 100 |
| Silicone treated lithium-dope barium sulfate | 10 |
| Spherical polymethyl methacrylate resin powder | 5 |
| Spherical silicone elastic powder | 2 |
| Spherical polyurethane elastic powder | 3 |
| Aluminum stearate treated fine particle titanium oxide | 6 |
| Silica covering zinc oxide | 4 |
| Silicone treated titanium oxide | 10 |
| Silicone treated ferric oxide | 1.2 |
| Silicone treated yellow iron oxide | 2.5 |
| Silicone treated black iron oxide | 0.9 |
| Paraben | proper quantity |
| Dimethylpolysiloxane | 4 |
| Methyl phenyl polysiloxane | 3 |
| Octhyl methoxy Cinnamate | 3 |
| Polyether silicone | 2 |
| Anti-oxidant | proper quantity |
| Perfume | proper quantity |

(Process)

The aforementioned powder all ingredients were mixed with a Henschel mixer, a total mixture of oily phase ingredients warmed to 80° C. was added using a spraying nozzle, and this was stirred to mix for 10 minutes. Thereafter, the material was allowed to stand to cool to 40° C., taken out, and ground with a grinding machine twice to prepare a powdery foundation.

Embodiment 17 Powdery foundation

| (prescription) | wt % |
|---|---|
| Fluorine modified silicone treated synthesis mica | too 100 |
| Fluorine modified silicone treated talc | 13 |
| Fluorine modified silicone treated sodium-dope barium sulfate | 15 |

-continued
Embodiment 17 Powdery foundation

| (prescription) | wt % |
|---|---|
| Spherical nylon powder | 7 |
| Spherical silicone elastic powder | 2 |
| Spherical polyurethane elastic powder | 1 |
| Fluorine modified silicone treated fine particle titanium oxide | 10 |
| Silicone treated titanium oxide | 9 |
| Silicone treated ferric oxide | 1.4 |
| Silicone treated yellow iron oxide | 2.8 |
| Silicone treated black iron oxide | 1.0 |
| Silica covering zinc oxide | 5 |
| Paraben | proper quantity |
| Dimethylpolysiloxane | 4 |
| methyl phenyl polysiloxane | 1 |
| Octhyl methoxy Cinnamate | 3 |
| Polyether silicone | 2 |
| Vaseline | 1 |
| Anti-oxidant | proper quantity |
| Perfume | proper quantity |

(Process)

The aforementioned powder all ingredients were mixed with a Henschel mixer, a total mixture of oily phase ingredients warmed to 80° C. was added using a spraying nozzle, and this was stirred to mix for 10 minutes. Thereafter, the material was allowed to stand to cool to 40° C., taken out, and ground with a grinding machine two times to prepare a powdery foundation.

Embodiment 18 Face powder (White powder)

| (prescription) | wt % |
|---|---|
| Zinc-dope barium sulfate | 35 |
| Porous plate-like silica | 5 |
| Metal soap treated talc | too 100 |
| Boron nitride | 7 |
| Silica covering zinc oxide | 3 |
| Ferric oxide | 0.3 |
| Yellow iron oxide | 1.2 |
| Spherical silicone powder | 5 |
| Vaseline | 1 |
| Squalane | 2 |
| Ester oil | 1 |
| Dimethylpolysiloxane | 1 |
| Paraben | proper quantity |
| Anti-oxidant | proper quantity |
| Perfume | proper quantity |

(Process)

The aforementioned powder all ingredients were mixed with a Henschel mixer, a total mixture of oily phase ingredients warmed to 80° C. was added using a spraying nozzle, and this was stirred to mix for 5 minutes. Thereafter, the material was allowed to stand to cool to 40° C., taken out, and ground with a grinding machine two times to prepare a face powder.

Embodiment 19 Loose powder (powdery white powder)

| (prescription) | Wt % |
|---|---|
| Talc | too 100 |
| Synthesis mica | 10 |
| Zinc-dope barium sulfate | 25 |
| Spherical porous silica powder | 5 |
| Spherical alumina powder | 5 |
| Zinc white | 3 |
| Silica covering zinc oxide | 5 |
| Squalane | 3 |
| Paraben | proper quantity |
| Perfume | proper quantity |

(Process)

The aforementioned powder all ingredients were mixed with a Henschel mixer, a total mixture of oily phase ingredients warmed to 80° C. was added using a spraying nozzle, and this was stirred to mix for 5 minutes. Thereafter, the material was allowed to stand to cool to 40° C., taken out, and ground with a grinding machine two times to prepare a loose powder.

Embodiment 20 O/W type emulsified cream foundation

| (prescription) | Wt % |
|---|---|
| Sericite | 7 |
| Silicic acid anhydride covering zinc oxide | 8 |
| Zinc-dope barium sulfate | 20 |
| Ferric oxide | 0.3 |
| Yellow iron oxide | 1.2 |
| Black iron oxide | 0.6 |
| Spherical polyethylene powder | 6 |
| Squalane | 10 |
| Olive oil | 10 |
| Stearic acid | 2 |
| Glycerin monostearate | 2 |
| Sorbitan POE (40) monostearate | 2 |
| Glycerol | 5 |
| Triethanolamine | 0.8 |
| pH modifier | proper quantity |
| Antiseptics | proper quantity |
| Ion exchanged water | too 100 |

(Process)

A powder was dispersed in water phase ingredients, and separately warmed oily phase ingredients were added to emulsify them at 85° C. At completion of emulsification, the material was cooled to room temperature, and charged into a container to obtain a cream foundation.

Embodiment 21 O/W type emulsified makeup foundation

| (prescription) | Wt % |
|---|---|
| Glycerol | 20 |
| Pentane 1,2-diol | 3 |
| 1,3-butylene glycol | 1 |
| Liquid paraffin | 7.5 |
| Isostearic acid | 0.5 |
| Medicine | 0.3 |
| Di 2-ethylhexyl phthalate | 0.3 |
| Spherical silica | 4 |
| Zinc-dope barium sulfate | 5 |
| Stabilizer | proper quantity |
| Perfume | proper quantity |
| Ion exchanged water | too 100 |

(Process)

A powder was dispersed in water phase ingredients, and separately warmed oily phase ingredients were added to emulsify them at 85° C. At completion of emulsification, the material was cooled to room temperature, and charged into a container to obtain a cream foundation.

Embodiment 22 W/O type emulsified liquid foundation

| (prescription) | Wt % |
| --- | --- |
| Silicone treated zinc-dope barium sulfate | 15 |
| Silicone treated titanium oxide | 8 |
| Silicone treated ferric oxide | 1.2 |
| Silicone treated yellow iron oxide | 2.6 |
| Silicone treated black iron oxide | 0.6 |
| Spherical silicone elastic powder | 2 |
| Spherical polymethyl methacrylate powder | 5 |
| Octyl silane treated fine particle titanium oxide | 6 |
| Cyclomethylsilicone | too 100 |
| Dimethylpolysiloxane | 4 |
| Squalane | 3 |
| Polyether modified silicone | 2 |
| Sorbitan sesqui isostearate | 1 |
| Dispersant | proper quantity |
| Dipropylene glycol | 2 |
| Ion exchange water | 20 |
| Paraben | proper quantity |
| Anti-oxidant | proper quantity |
| Perfume | proper quantity |

(Process)

All oil phase ingredients were warmed to 85° C. dissolved and dispersed, and separately warmed water phase ingredients were added to emulsify them at 85° C. At completion of emulsification, the material was cooled to room temperature, and charged into a container to obtain a liquid foundation.

Embodiment 23 W/O type emulsified liquid foundation

| (prescription) | Wt % |
| --- | --- |
| Fluorine modified silicone treated mica | 5 |
| Fluorine modified silicone treated sericite | 7 |
| Fluorine modified silicone treated titanium oxide | 12 |
| Fluorine modified silicone treated iron oxide | 4 |
| Fluorine modified silicone treated zinc-dope barium sulfate | 6 |
| Octylsilane treated fine particle titanium oxide | 4 |
| Spherical polymethyl methacrylate powder | 5 |
| Spherical silicone elastic powder | 5 |
| Silica covering zinc oxide | 4 |
| Cyclomethylsilicone | too 100 |
| Dimethylpolysiloxane | 4 |
| Squalane | 3 |
| Polyether modified silicone | 1 |
| Fluorine modified polyether modified silicone | 3 |
| Dispersion auxiliary | proper quantity |
| Dipropylene glycol | 2 |
| Ion exchanged water | 20 |
| Paraben | proper quantity |
| Antioxidant | proper quantity |
| Perfume | proper quantity |

(Process)

All oil phase ingredients were warmed to 85° C. dissolved and dispersed, and separately warmed water phase ingredients were added to emulsify them at 85° C. At completion of emulsification, the material was cooled to room temperature, and charged into a container to obtain a liquid foundation.

Embodiment 24 Oily eyes shadow

| (prescription) | Wt % |
| --- | --- |
| Dimethylsilicone | 10 |
| Ester oil | 10 |
| Liquid paraffin | too 100 |
| Squalane | 10 |
| Sorbitan sesqi isostearate | 1 |
| Polyethylene wax | 8 |
| Ceresin wax | 3 |
| Mica | 7 |
| Spherical cellulose powder (about 6 μm) | 5 |
| Zinc-dope barium sulfate | 25 |
| Anti-oxidant | proper quantity |
| Perfume | proper quantity |

(Process)

A mixture of an oily phase and powdery ingredients was warmed to 85° C. to melt and disperse it, and this was degassed, and charged into an intermediate dish to prepare an oily eyes shadow.

Embodiment 25 Lipstick

| (prescription) | Wt % |
| --- | --- |
| Octhyl methoxy cinnamate | 5 |
| Polyethylene wax | 10 |
| Ceresin wax | 3 |
| Lanolin | 20 |
| Polybutene | 20 |
| Dimethylsilicone | 12 |
| Ester oil | too 100 |
| Titanium oxide | 4.5 |
| Red 201 | 0.5 |
| Red 202 | 1.1 |
| Red 223 | 0.3 |
| Spherical polyethylene powder (about 5 μm) | 2 |
| Zinc-dope barium sulfate | 5 |
| Red interference pearl agent | 5 |
| Antioxidant | proper quantity |
| Perfume | proper quantity |

(Process)

A mixture of an oily phase and powdery ingredients was warmed to 85° C. to melt and disperse it, and this was degassed, and charged into an mold to prepare an lip stick.

Using the insoluble powder of the present invention, the skin barrier function recovering powder with excellent skin roughening preventing and improving effect and skin external composition can be obtained.

What is claimed is:

1. A method for recovering barrier function in a skin, comprising:
    applying to an effective amount of a skin external composition comprising 1-40% by weight of an insoluble powder having a negative value of zeta-potential measured in Tris-HCl buffer at pH 7.5 and a main ingredient of barium sulfate doped with a metal ion;
    wherein said powder has an average primary particle diameter of 3 to 100 μm and aspect ratio of 3 to 250; and
    wherein said metal ion is one selected from the group consisting of lithium, sodium and zinc.

2. A method for preventing roughness and improving conditions of a skin comprising:

applying to an effective amount of a skin external composition comprising 1-40% by weight of an insoluble powder having a negative value of zeta-potential measured in Tris-HCl buffer at pH 7.5 and a main ingredient of barium sulfate doped with a metal ion;

wherein said powder has an average primary particle diameter of 3 to 100 μm and aspect ratio of 3 to 250; and wherein said metal ion is one selected from the group consisting of lithium, sodium and zinc.

3. The method for recovering barrier function in a skin according to claim 1, wherein said barium sulfate doped with a metal ion is obtained by mixing a barium compound solution containing a barium ion and a metal salt compound solution containing a metal ion, and adding the mixture to a sulfate compound solution containing a sulfate ion.

4. The method for recovering barrier function in a skin according to claim 3, wherein the barium ion, the sulfate ion and the metal ion has a mole ratio of 1 to 0.5-2.0 to 0.001-10.

5. The method for preventing roughness and improving conditions of a skin according to claim 2, wherein said barium sulfate doped with a metal ion is obtained by mixing a barium compound solution containing a barium ion and a metal salt compound solution containing a metal ion, and adding the mixture to a sulfate compound solution containing a sulfate ion.

6. The method for preventing roughness and improving conditions of a skin according to claim 5, wherein the barium ion, the sulfate ion and the metal ion has a mole ratio of 1 to 0.5-2.0 to 0.001-10.

* * * * *